United States Patent
Nukina et al.

(10) Patent No.: US 6,840,926 B2
(45) Date of Patent: Jan. 11, 2005

(54) MULTI-LAYER FEMININE HYGIENIC PAD

(75) Inventors: Mica Nukina, 3-5-2-405, Miyamaedaira 1-chome, Miyamae-ku, Kawasaki-shi, Kanagawa-ken (JP); Mitsuru Uchiyama, Tokyo (JP); Mitsuko Uchiyama, Tokyo (JP); Mitsuo Ohtani, Kawachinagano (JP); Atsushi Uchiyama, Tokyo (JP)

(73) Assignee: Mica Nukina, Kawasaki (JP)

( * ) Notice: Subject to any disclaimer, the term of this patent is extended or adjusted under 35 U.S.C. 154(b) by 9 days.

(21) Appl. No.: 10/218,540

(22) Filed: Aug. 14, 2002

(65) Prior Publication Data

US 2003/0009142 A1 Jan. 9, 2003

Related U.S. Application Data

(62) Division of application No. 09/605,109, filed on Jun. 28, 2000, now Pat. No. 6,730,067, which is a division of application No. 08/791,564, filed on Jan. 31, 1997, now Pat. No. 6,171,425.

(30) Foreign Application Priority Data

Feb. 8, 1996 (JP) .......................... 1996-46674
May 8, 1996 (JP) ........................ 1996-137511

(51) Int. Cl.$^7$ ............................................. A61F 13/15
(52) U.S. Cl. ......................... 604/385.03; 604/385.01; 604/385.14
(58) Field of Search .................. 604/385.03, 385.14, 604/385.05, 385.01; 442/224, 238, 244, 278, 323, 373

(56) References Cited

U.S. PATENT DOCUMENTS

| | | | |
|---|---|---|---|
| 3,257,228 A | 6/1966 | Reed | |
| 3,570,492 A | 3/1971 | Bettencourt | |
| 3,666,611 A | 5/1972 | Joa | |
| 3,688,771 A | 9/1972 | Werner | |
| 3,984,272 A | 10/1976 | Teed | |
| 4,079,739 A | 3/1978 | Whitehead | |
| 4,184,902 A | 1/1980 | Karami | |
| 4,551,145 A | 11/1985 | Ryan | |
| 4,574,024 A | 3/1986 | VanMalderen | |
| 4,581,027 A | 4/1986 | Alvarado | |
| 4,801,494 A | * 1/1989 | Datta et al. | 442/352 |
| 5,160,564 A | 11/1992 | Hasegawa et al. | |
| 5,344,808 A | 9/1994 | Watanabe et al. | |
| 5,429,631 A | 7/1995 | Grenier | |
| 5,599,339 A | 2/1997 | Horney | |
| 5,706,950 A | 1/1998 | Houghton et al. | |
| 5,720,738 A | * 2/1998 | Clark | 604/385.01 |
| 5,824,172 A | 10/1998 | Kielpikowski | |
| H1788 H | 2/1999 | Christon et al. | |
| 5,910,137 A | 6/1999 | Clark et al. | |
| 6,013,064 A | * 1/2000 | Yamada | 604/385.01 |
| 6,040,267 A | 3/2000 | Mano et al. | |

FOREIGN PATENT DOCUMENTS

| | | |
|---|---|---|
| EP | 0 684 029 | 11/1995 |
| GB | 863582 | 3/1961 |
| JP | 6-121812 | 5/1994 |
| WO | WO 95/29655 | 11/1995 |

* cited by examiner

Primary Examiner—Jacqueline Stephens
(74) Attorney, Agent, or Firm—Frishauf, Holtz, Goodman & Chick, P.C.

(57) ABSTRACT

A multi-layer feminine hygienic pad comprising a laminate of two or more composite absorption sheets in which an upper composite absorption sheet which comprises an upper backing sheet laminated to a back side thereof is laid on top of a lower composite absorption sheet comprising a lower backing sheet laminated to a back side thereof such that the back side of the upper composite absorption sheet is placed downward and peripheral parts of the lower backing sheet and the upper backing sheet are temporarily attached together by a high pressure pressing without using an adhesive and, a back side of a lowest backing sheet of a lowest composite absorption sheet is capable of being attachable to underwear. The composite absorption sheet and the backing sheet are approximately the same size.

16 Claims, 8 Drawing Sheets

MULTI-LAYER FEMININE HYGIENIC PAD

CROSS-REFERENCE TO RELATED APPLICATIONS

This is a Divisional application of application Ser. No. 09/605,109, filed Jun. 28, 2000 now U.S. Pat. No. 6,730,067, which is a Divisional application of application Ser. No. 08/791,564, filed Jan. 31, 1997 (now U.S. Pat. No. 6,171,425).

BACKGROUND OF THE INVENTION

1. Field of the Invention

The present invention relates to a feminine hygienic pad which is convenient for use.

2. Background Information

There is the general tendency that a feminine hygienic pad is replaced with a new pad at the time of using a toilet even when the sheet of a fluid-absorbing material still has the absorbing ability, and the used pad is disposed.

Development of feminine hygienic pads has mainly been focused on increasing the ability to absorb fluid. However, further increase in this ability is rather meaningless when the above tendency is taken into consideration.

In order to replace a feminine hygienic pad every time using a toilet, several pads must be brought along as replacements when traveling outside the home. Several pads are rather bulky although recent pads are made compact, and this situation causes inconvenience.

Therefore, when women are dressed in a fashionable manner such as in a formal manner, to carry several pads necessitates the carrying of a handbag large enough to carry several pads.

Young women such as student girls who feel shyness to a large extent tend to dislike using a toilet for a long time. However, taking feminine hygienic pads with them to school or on a trip causes inconvenience with respect to the place for keeping the pads and the place and time for replacing the pads in a limited time and space.

Accordingly, the present invention has an object of providing a multi-layer feminine hygienic pad which does not require bringing many pads along as replacements, reduces the troublesome handling to attach the pad to a desired place of an underwear to once with a plurality of composite absorption sheets, and can reduce the time necessary for replacing a used composite absorption sheet with a fresh sheet to a great extent. The present invention also has an object of providing a process for producing the above multi-layer feminine hygienic pad.

SUMMARY OF THE INVENTION

The present invention takes into account the following: sheets for absorption of fluid can be made very thin and have a great absorbing ability because of the progress in the fluid-absorbing materials made of water-absorbing macromolecular compounds; even when 2 to 5 sheets of the fluid-absorbing material are laminated together in conventional feminine hygienic pads which are disposed after a single use of a package, the thickness of the laminate is not much increased and the feeling during the use and the appearance do not change much because the sheet of a fluid-absorbing material is very thin before it absorbs fluid; and when 2 to 5 conventional sheets of a fluid-absorbing material are laminated together in the condition that they are separated from each other, an entirely fresh feminine hygienic layer can be exposed by simply peeling off the sheet of a fluid-absorbing material at the upper layer after use, and the same condition as that of a new feminine hygienic pad can be brought about in a short time. The result can be that the effect corresponding to attaching 2 to 5 packages of a conventional feminine hygienic pad can be realized by attaching a single package of the feminine hygienic pad and the necessity of bringing along replacement packages of feminine hygienic pads is eliminated. To attain the inventive objects, a multi-layer feminine hygienic pad is provided which comprises a laminate sheet containing sheets of a fluid-absorbing material, enables easy removal of the used upper sheet of the fluid-absorbing material, and can conveniently be produced. A process for producing this multi-layer feminine hygienic pad is also provided.

Sheets of fluid-absorption having a multi-layer structure are known for increasing the absorbed amount or to prevent leaking at the sides of the pads. However, a structure which prevents permeation of a fluid absorbed at an upper layer into a sheet of a fluid-absorbing material laminated at lower layers is not known. In other words, the laminate structure in which individual layers of fluid-absorption are separated with separating layers which do not allow invasion of fluid, and which enables peeling off a layer from another layer easily by fingers although the individual layers are firmly fixed to their own positions, has not been known.

Accordingly, the present invention provides:

(1) A multi-layer feminine hygienic pad comprising: a laminate of two or more composite absorption sheets in which an upper composite absorption sheet comprising a sheet of a fluid-absorbing material and an upper backing sheet laminated to the lower side of the sheet of a fluid-absorbing material is laid on top of a lower composite absorption sheet comprising a sheet of a fluid-absorbing material and a lower backing sheet which has a dimension larger than the dimension of the sheet of a fluid-absorbing material and is laminated to the lower side of the sheet of a fluid-absorbing material, and peripheral part of the lower backing sheet outside the area of the sheet of a fluid-absorbing material of the lower composite absorption sheet and peripheral part of the upper backing sheet of the upper composite absorption sheet are temporarily attached together at least at two opposite edges of the peripheral parts; and a release film coated with a pressure-sensitive adhesive and attached to the lower side of a backing sheet of a lowest composite absorption sheet;

(2) A multi-layer feminine hygienic pad described in (1) wherein the peripheral part of the lower backing sheet of the lower composite absorption sheet and the peripheral part of the upper backing sheet of the upper composite absorption sheet are temporarily attached together with a layer of a pressure-sensitive adhesive disposed between the peripheral parts by pressing the peripheral parts to each other;

(3) A multi-layer feminine hygienic pad described in (2) wherein the layer of a pressure-sensitive adhesive is disposed on the lower side of upper composite absorption sheet;

(4) A multi-layer feminine hygienic pad described in (2) wherein a layer of a releasing agent is disposed between the layer of a pressure-sensitive adhesive and the peripheral part of the lower backing sheet of the lower composite absorption sheet;

(5) A multi-layer feminine hygienic pad described in (1) wherein the lower backing sheet and the upper backing sheet are each made of a thermoplastic resin, and the peripheral part of the lower backing sheet of the lower composite absorption sheet and the peripheral part of the upper backing sheet of the upper composite absorption sheet are temporarily attached together by intermediate melt adhesion using an agent for preventing melt adhesion disposed between the peripheral parts;

(6) A multi-layer feminine hygienic pad described in (5) wherein the intermediate melt adhesion is made by melt cutting using a heated blade;

(7) A multi-layer feminine hygienic pad described in (1) wherein whole or a portion of the peripheral part of the lower backing sheet of the lower composite absorption sheet and whole or a portion of the peripheral part of the upper backing sheet of the upper composite absorption sheet are temporarily attached together with a layer of a heat-sensitive adhesive disposed between the peripheral parts by heat pressing the peripherals parts to each other;

(8) A multi-layer feminine hygienic pad described in (1) wherein the upper backing sheet of the upper composite absorption sheet and the lower backing sheet of the lower composite absorption sheet forming the laminate of two or more composite absorption sheets are made of a single continuous sheet which is folded at the boundary line of the upper backing sheet and the lower backing sheet and has two perforation lines in the vicinity of the boundary line;

(9) A multi-layer feminine hygienic pad described in (8) wherein the upper side of the lower composite absorption sheet and the lower side of the upper composite absorption sheet are temporarily attached together with an adhesive material along edges of the lower absorption sheet and the upper composite absorption sheet opposite to the folded boundary line;

(10) A multi-layer feminine hygienic pad described in (1) wherein the backing sheets of the composite absorption sheets are temporarily attached together in a manner that the backing sheets of the composite absorption sheets which are all laid on top of another are completely attached to each other by heat sealing at least at two opposite edges of the peripheral parts of the backing sheets, and perforation lines are formed at inner parts along all heat sealed parts so that the completely attached backing sheets can be separated from each other at the perforation lines;

(11) A multi-layer feminine hygienic pad described in (1) wherein the peripheral part of the lower backing sheet of the lower composite absorption sheet and the peripheral part of the upper backing sheet of the upper composite absorption sheet are temporarily attached together at least at two opposite edges of the peripheral parts by pressing the edges to each other by a large mechanical pressure;

(12) A multi-layer feminine hygienic pad described in (11) wherein the peripheral part of the lower backing sheet and the peripheral part of the upper backing sheet have protrusions and depressions formed by pressing the peripheral parts by a press and are temporarily attached together by fitting the protrusions and the depressions of the lower backing sheet to the depressions and the protrusions of the upper backing sheet, respectively;

(13) A multi-layer feminine hygienic pad comprising: a laminate of two or more composite absorption sheets in which the composite absorption sheet comprises a sheet of a fluid-absorbing material and a backing sheet having approximately the same dimension as the dimension of the fluid-absorbing material, and whole or a portion of the lower side of an upper backing sheet of an upper composite absorption sheet is temporarily attached to the upper side of a lower composite absorption sheet; and a release film coated with a pressure-sensitive adhesive and attached to the lower side of a backing sheet of the lowest composite absorption sheet;

(14) A multi-layer feminine hygienic pad described in (13) wherein whole or a portion of the lower side of the upper composite absorption sheet is coated with a heat-sensitive adhesive or a pressure-sensitive adhesive having a small adhesive strength, and the composite absorption sheets are temporarily attached together with a layer of the adhesive;

(15) A multi-layer feminine hygienic pad comprising a laminate of two or more composite absorption sheets in which the composite absorption sheet comprises a sheet of a fluid-absorbing material and a backing sheet laminated to the lower side of the fluid absorbing material, each backing sheet has a peripheral part which is extended from periphery of a backing sheet of another composite absorption sheet disposed directly below, a combined extended peripheral part is formed by the successively extended peripheral parts of the backing sheets, the lower side of the combined extended peripheral part of the backing sheets and the lower side of a backing sheet of a lowest composite absorption sheet are each coated with a layer of a pressure-sensitive adhesive, and whole layers of a pressure-sensitive adhesive are covered with a single sheet of a release film to form a laminate integrally fixed by the single sheet of a release film;

(16) A composite absorption sheet for a multi-layer feminine hygienic pad comprising a composite absorption sheet and a film which is laminated to the lower side of the composite absorption sheet, has an opening, and contains the composite absorption sheet by turning inside out;

(17) A process for producing a multi-layer feminine hygienic pad which continuously produces the multi-layer feminine hygienic pad by using two or more long sheets of a thermoplastic resin for backing sheet, two or more long sheets of a porous film of a thermoplastic resin, and two or more sheets of a fluid-absorbing macromolecular compound as materials and comprises continuously laying the long sheet of a thermoplastic resin for backing sheet on the upper side of the long sheet of a porous film of a thermoplastic resin, pressing side edge parts of the two long sheets which have been laid together and an adhesive disposed between the side edge parts of the long sheets to each other to prepare a temporarily attached laminate sheet, laying a plurality of the temporarily attached laminate sheets thus prepared on top of another with the sheets of a fluid-absorbing macromolecular compound disposed between the laminate sheets, and heat sealing or melt cutting side edges of the laminate sheets to form an intermediate melt adhesion between the long sheets in the same laminate sheet and to heat seal a long sheet of a thermoplastic resin for backing sheet in one laminate sheet to a long sheet of a porous film of a thermoplastic resin in another laminate sheet disposed directly below and a long sheet of a porous film of a thermoplastic resin in one laminate sheet to a long sheet of a thermoplastic for backing sheet in another laminate sheet disposed directly above;

(18) A process for producing a multi-layer feminine hygienic pad which continuously produces the multi-layer feminine hygienic pad by using two or more long sheets of a thermoplastic resin for backing sheet, two or more long sheets of a porous film of a thermoplastic resin, and two or more long sheets of a fluid-absorbing macromolecular compound as materials and comprises continuously laying the long sheet of a thermoplastic resin for backing sheet on the upper side of the long sheet of a porous film of a thermoplastic resin, pressing side edge parts of the two long sheets which have been laid together and an adhesive disposed between the side edge parts of the long sheets to each other to prepare a temporarily attached laminate sheet, laying a plurality of the temporarily attached laminate sheets thus prepared and a plurality of the long sheets of a fluid-absorbing material having a narrower width than the width of the temporarily attached laminate sheet alternately on top of another to prepare an alternating laminate sheet, laminating one long sheet of a porous film of a thermoplastic resin for an upper surface to the upper side of the uppermost layer of the alternating laminate sheet and one long backing sheet of a thermoplastic resin for a lower surface to the lower side of the lowest layer of the alternating laminate to prepare a long multi-layer laminate sheet containing a prescribed number of the sheet of a fluid-absorbing macromolecular compound, heat sealing or melt cutting side edges of the long multi-layer laminate sheets to heat seal a long sheet of a thermoplastic resin for backing sheet in one laminate sheet to a long sheet of a porous film of a thermoplastic resin in another laminate sheet disposed directly below or to the long backing sheet of a thermoplastic resin for a lower surface disposed directly below and a long sheet of a porous film of a thermoplastic resin in one laminate sheet to a long sheet of a thermoplastic resin for backing sheet in another laminate sheet disposed directly above or to the long sheet of a porous film of a thermoplastic resin for an upper surface disposed directly above and to form an intermediate melt adhesion between the long sheets in the same laminate sheet by the heat sealing or melt cutting in the presence of an adhesive, and cutting the thus prepared long multi-layer laminate to a prescribed length;

(19) A process described in (18) wherein the sheet of a fluid-absorbing macromolecular compound is a fabric;

(20) A process for producing a multi-layer feminine hygienic pad comprising preparing a temporarily attached laminate sheet by continuously laying a long sheet of a porous film of a thermoplastic resin on the upper side of a long sheet of a thermoplastic resin for backing sheets and then by pressing the two long sheets together with an adhesive disposed between the two long sheets, coating another long sheet of a thermoplastic resin for backing sheet with a pressure-sensitive adhesive on the lower side and attaching a release film made of a thermoplastic resin on the coated side of the sheet, disposing sheets of a fluid-absorbing macromolecular compound having a width smaller than the width of the temporarily attached laminate sheet and a prescribed length on the long sheet of a thermoplastic resin for backing sheet attached with a release film at positions separated by a prescribed distance in a manner that the longitudinal direction of the sheets of a fluid-absorbing macromolecular compound is parallel with or perpendicular to the longitudinal direction of the long sheet, laying the temporarily attached laminate sheet on the long sheet of a thermoplastic resin for backing sheet on which the sheets of a fluid-absorbing macromolecular compound have been disposed, disposing sheets of a fluid-absorbing macromolecular compound having the same size as that described above at positions separated by the prescribed distance in a manner that the sheets of a fluid-absorbing macromolecular compound are placed over the corresponding sheets on the long sheet disposed below, optionally repeating the steps of laminating the temporarily attached laminate sheet and disposing the absorbing sheets of a macromolecular compound having the same size as that described above one or more times, laminating a long sheet of a porous film of a thermoplastic resin on the uppermost layer to prepare a long composite laminate sheet having a prescribed number of the sheet of a fluid-absorbing macromolecular compound, continuously feeding the thus prepared long composite laminate sheet to a table of a heat sealing process, attaching the temporarily attached laminate sheets in the long composite laminate sheet to each other by heat sealing or melt cutting at edges outside the sheets of a fluid-absorbing macromolecular compound, and finally melt cutting or pressing under heating followed by mechanically cutting the thus worked long composite laminate sheet at positions between the sheets of a fluid-absorbing macromolecular compound disposed inside the long composite laminate sheet to separate the long composite laminate sheet into pieces each containing one sheet of a fluid-absorbing macromolecular compound; and

(21) A process for producing a multi-layer feminine hygienic pad comprising preparing a temporarily attached laminate sheet by continuously laying a long sheet of a porous film of a thermoplastic resin on the upper side of a long sheet of a thermoplastic resin for backing sheet and then by pressing the two long sheets together with an adhesive disposed between the two long sheets, disposing sheets of a fluid-absorbing macromolecular compound having a width smaller than the width of the temporarily attached laminate sheet and a prescribed length on another long sheet of a thermoplastic resin for backing sheet at positions separated by a prescribed distance in a manner that the longitudinal direction of the sheets of a fluid-absorbing macromolecular compound is parallel with or perpendicular to the longitudinal direction of the long sheet, laying the temporarily attached laminate sheet on the long sheet of backing sheet on which the sheets of a fluid-absorbing macromolecular compound have been disposed, disposing sheets of a fluid-absorbing macromolecular compound having the same size as that described above at positions separated by a prescribed distance in a manner that the sheets of a fluid-absorbing macromolecular compound are placed over the corresponding sheets on the long sheet disposed below, optionally repeating the steps of laminating the temporarily attached laminate sheet and disposing the absorbing sheets of a macromolecular compound having the same size as that described above one or more times, laminating a long sheet of a porous film of a thermoplastic resin on the uppermost layer to prepare a long composite laminate sheet having a prescribed number of the sheet of a fluid-absorbing macromolecular compound, continuously feeding the thus prepared long composite laminate sheet to a table of a heat sealing process, attaching the temporarily attached laminate sheets in the long composite laminate sheet to each other by heat sealing or melt cutting at edges outside the sheets of a fluid-absorbing macromolecular compound, attaching a long sheet of a release film of a thermoplastic resin coated with a pressure-sensitive adhesive at the central part of the lower side of the prepared long composite laminate sheet before or after the step of heat sealing, and finally melt cutting or pressing under heating followed by mechanically cutting the thus worked long composite laminate sheet at positions between the sheets of a fluid-absorbing macromolecular compound disposed inside the long composite laminate sheet to separate the long composite laminate sheet into pieces each containing one sheet of a fluid-absorbing macromolecular compound.

A multi-layer feminine hygienic pad comprising a laminate of two or more composite absorption sheets in which an upper composite absorption sheet which comprises an upper backing sheet laminated to a back side thereof is laid on top of a lower composite absorption sheet which comprises a lower backing sheet laminated to a back side thereof. The composite absorption sheet and the backing sheet are approximately the same size. The back side of the upper composite absorption sheet is placed downward and a peripheral part of the lower backing sheet and a peripheral part of the upper backing sheet are temporarily attached together by high pressure pressing the peripheral part of the lower backing sheet and the peripheral part of the upper backing sheet without using an adhesive, and a back side of a lowest backing sheet of a lowest composite absorption sheet is capable of being attachable to underwear.

Figure 1:
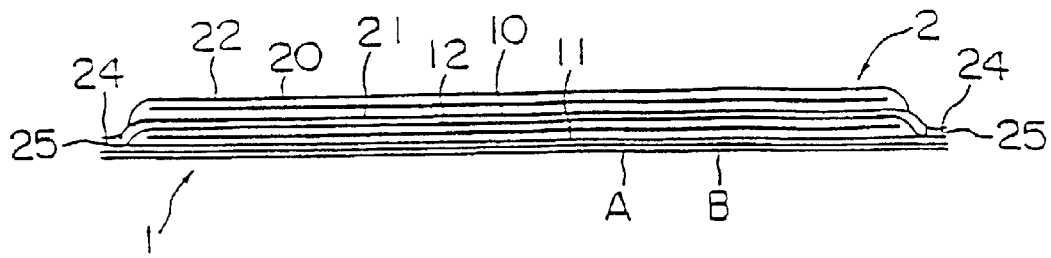
FIG. 1 shows a sectional view of a multi-layer feminine hygienic pad as an embodiment of the present invention.

The numbers and characters in the figures have the meanings as listed in the following:

| | |
|---|---|
| 1, 2, 3, 4, and 5: | composite absorption sheets |
| 10, 20, 30, and 40: | sheets of a fluid-absorbing material |
| 11, 21, 31, 41, and 51: | backing sheets |
| 12, 22, 32, 42 and 52: | a face film |
| 24: | a peripheral part |
| 25, 35, and 45: | pressure-sensitive adhesives at peripheral parts |
| 26: | a protruded tongue |
| 27: | a extended tongue |
| 28: | a extended tongue |
| A: | a layer of a pressure-sensitive adhesive |
| B: | a release film |
| C: | a heat sealed part |
| D: | a boundary line |
| E: | a perforation line |
| F: | a mechanically pressed part |
| G: | a row of depressions |
| H: | an integrally heat sealed part of all layers |
| K: | a temporarily attached part |
| m: | a tongue |
| n: | a tongue |
| M: | a laminate sheet |
| N: | an end part formed by cutting |
| S: | a slit on a packaging film |
| R: | a packaging film |

DETAILED DESCRIPTION OF THE INVENTION

As for the sheet of a fluid-absorbing material used in the present invention, materials, shapes, and structures used in fluid-absorbing sheets of conventional feminine hygienic pads can be used without any particular restrictions.

As the material used in the sheet of a fluid-absorbing material, a material having a large absorbing ability with a small thickness, such as a fabric or a non-woven fabric made of a generally known water-absorbing macromolecular compound or cotton, can advantageously be used.

A feminine hygienic pad generally has the following structure: a sheet of a fluid-absorbing material is placed on a backing sheet; a sheet to prevent backward transfer of the absorbed fluid is laminated on the sheet of a fluid-absorbing material; a porous film is laminated on this combined sheet; peripheral parts of the porous film is fixed to peripheral parts of the backing sheet by adhesion, heat sealing, or the like method; and thus the sheet of a fluid-absorbing material is contained between the backing sheet and the porous films disposed below and above the sheet of a fluid-absorbing material, respectively.

In the present invention, the sheet of a fluid-absorbing material and the backing sheet on which the sheet of a fluid-absorbing material is disposed are essential components. However, the laminate structure having the porous film which is disposed on the sheet of a fluid-absorbing material is not essential, and other structures can also be used in the present invention. Therefore, in the present invention, any sheet comprising the combination of a backing sheet and a sheet of a fluid-absorbing material disposed on the backing sheet is defined as a composite absorption sheet. When a backing sheet has a larger dimension than that of a sheet of a fluid-absorbing material, peripheral parts of the backing sheet are extended outside the sheet of a fluid-absorbing material. In this case, the upper side of the peripheral parts of the backing sheet sometimes remains exposed without being laminated with a porous face film or the like. However, the peripheral parts of the combined sheets are regarded as the peripheral parts of the backing sheet, including the case described above. The surface of a face sheet integrally attached to the upper side of peripheral parts of the backing sheet is also regarded as the surface of the backing sheet.

In the present invention, it is particularly advantageous that a packaging sheet for disposal is attached to the composite absorption sheet, particularly to the backing sheet of the composite absorption sheet because the packaging sheet can contain a used upper composite absorption sheet when the used sheet is removed for disposal, and no other container is available. For example, when perforation is formed at the central part of a film laminated to the backing sheet as an inlet of a container, or a film attached to the backing sheet has an edge which is left unattached to the backing sheet and used as an inlet of a container, the main part of the composite absorption sheet can be contained in the film by turning the film inside out over the composite absorption sheet.

Therefore, the composite absorption sheet of the present invention may be, for example, a laminate having the minimum construction composed of a backing sheet and a sheet of a fluid-absorbing material laminated to the backing sheet or a composite sheet comprising a backing sheet, a sheet of a fluid-absorbing material, a sheet for preventing backward transfer of the fluid, a porous film, and other functional sheets which are laminated together.

The porous film means a sheet which allows permeation of fluid. The concept of the porous film in the present invention includes films having numerous fine pores as well as films which can allow permeation of fluid without resistance even when the film does not have numerous fine pores, such as a paper sheet showing good permeation of fluid. As the porous film used in the present invention, a thermoplastic film is preferable in view of the permeability of fluid and the processability.

A preferable embodiment of the feminine hygienic pad of the present invention is a laminate comprising two or more composite absorption sheets which are the lowest composite absorption sheet, a second composite absorption sheet disposed above the lowest composite absorption sheet which is temporarily attached to the lowest composite absorption sheet by temporarily attaching a peripheral part to an extended peripheral part of the lowest absorbing sheet, a third composite absorption sheet disposed above the second composite absorption sheet in the same manner, and the like composite absorption sheets temporarily attached successively. When the backing sheet has an approximately the same dimension as that of the sheet of a fluid-absorbing material, a laminate of two or more composite absorption sheets can be formed by temporarily attaching a peripheral part of the upper side of a lower composite absorption sheet to a peripheral part of the lower side of an upper composite absorption sheet.

In the present invention, the temporary attachment of a lower composite absorption sheet and an upper composite absorption sheet means the condition in which the composite absorption sheets are firmly attached together while the feminine hygienic pad is brought along and used, and the upper composite absorption sheet can easily be detached from the lower composite absorption sheet by fingers to replace the used upper composite absorption sheet with the fresh lower composite absorption sheet. In this condition, the used composite absorption sheet at the uppermost layer can be detached by peeling with fingers while the backing sheet in the lowest composite absorption sheet of the feminine hygienic pad of the present invention is kept attached to the underwear.

In another embodiment of the present invention, an upper composite absorption sheet and a lower composite absorption sheet are temporarily attached together not only between the peripheral parts but also directly between the whole lower surface or the central part of the lower side of the upper composite absorption sheet and the upper side of the lower composite absorption sheet by using an adhesive or by pressing to each other by a high pressure. As the adhesive used for this purpose, a heat-sensitive adhesive is preferable because the surface of the lower composite absorption sheet is not sticky after the upper composite absorption sheet has been removed.

The above temporarily attached condition which enables subsequent removal can be achieved, for example, by fixing a peripheral part of the backing sheet extending from a sheet of a fluid-absorbing material or a peripheral part of an upper side of a sheet of a fluid-absorbing material of a lower composite absorption sheet to a peripheral part of a backing sheet of an upper composite absorption sheet by a weak binding force. When the temporary attachment is made at one edge of a composite absorption sheet alone, the relative position of layers in the laminate is unstable. Because the temporary attachment must be firmly kept during use, the temporary attachment is made at least at two opposite edges of the composite absorption sheets or along one half or more, preferably 75% or more, of the whole peripheral parts of the composite absorption sheets.

As the method of the temporary attachment, any method can be used as long as no adhesive property remains on the surface of the backing sheet of the lower composite absorption sheet when the temporary attachment is broken to remove the upper composite absorption sheet and the remaining lower composite absorption sheet is used. Examples of such a method include partial adhesion of a peripheral part alone of a composite absorption sheet with a pressure-sensitive adhesive which allows repeated adhesion and peeling; overall adhesion between the whole lower surface of an upper composite absorption sheet and the whole upper surface of a lower composite absorption sheet with a pressure-sensitive adhesive having a small adhesive strength; adhesion by heating and pressing using a heat-sensitive adhesive which does not allow repeated adhesion and peeling; intermediate melt adhesion of peripheral parts in the presence of an agent for preventing melt adhesion disposed between the parts; formation of a perforation which facilitates cutting a film and separating the film into parts; and ultra-high pressure adhesion which uses no adhesive, made by compression by a high pressure, and does not allow repeated adhesion and peeling. Two or more of the above methods may also be used in combination as the method of the temporary attachment of the present invention. For example, a method of temporarily attaching one edge by forming a perforation or by compression and temporarily attaching the opposite edge with a pressure-sensitive or heat-sensitive adhesive can advantageously be used.

The temporary attachment can generally be conducted at a peripheral part of a backing sheet which is extended from a peripheral part of a sheet of a fluid absorbing material. When the temporary attachment using a layer of a heat-sensitive adhesive or a layer of a pressure-sensitive adhesive having a small adhesive strength is used as the method of temporary attachment, the surface of a lower composite absorption sheet is not sticky after an upper composite absorption sheet has been removed, therefore the whole lower surface of the upper composite absorption sheet can be coated with the heat-sensitive adhesive or with the pressure-sensitive adhesive having a small adhesive strength and temporarily attached to the upper side of the lower composite absorption sheet. The above method of using a heat-sensitive adhesive or a pressure-sensitive adhesive having a small adhesive strength can be used even when there is no peripheral parts extended from a sheet of a fluid-absorbing material, for example, when a backing sheet has the same dimension as that of a sheet of a fluid-absorbing material in a composite absorption sheet.

In place of, or in addition to the temporary attachment of an upper composite absorption sheet to a lower composite absorption sheet, the lower side of a peripheral part of an upper composite absorption sheet which is extended from a peripheral part of a lower composite absorption sheet can temporarily be attached directly to a fabric of an underwear with a pressure-sensitive adhesive. When this method is used, the layers of a pressure-sensitive adhesive at the lower sides of the peripheral parts of backing sheets which are each extended outside the composite absorption sheet disposed below and the layer of a pressure-sensitive adhesive at the lower side of the backing sheet of the lowest composite absorption sheet can be protected with a single sheet of a release film until the feminine hygienic pad is used. This single sheet of a release film holds the whole multi-layer structure until the pad is used. Therefore, it is preferred that an additional method is used so that the sheets in the multi-layer feminine hygienic pad are not separated apart when the release film is removed.

In the feminine hygienic pad of the present invention, the mechanism for holding the composite absorption sheet to an underwear or the like and the mechanism for preventing backward transfer of fluid and side leaking of fluid are not particularly limited, and any conventional structure for feminine hygienic pads can be used without particular restriction as long as the objects of the present invention are not adversely affected.

In a preferable embodiment of the feminine hygienic pad of the present invention, the structure of the composite absorption sheet constituting the feminine hygienic pad is approximately the same as that of conventional feminine hygienic pads. The dimension of the backing sheet is larger than the dimension of the sheet of a fluid-absorbing material, and at least a part, preferably major parts, of the peripheral part of the backing sheet are extended outside the sheet of a fluid-absorbing material comprised in the composite absorption sheet.

On the lower side of the backing sheet of the lowest composite absorption sheet used in the present invention, a conventional mechanism for attachment, such as a layer of a pressure-sensitive adhesive, is disposed to fix the pad to a desired position of the fabric of an underwear.

A structure having a layer of a pressure-sensitive adhesive and a release film attached to the layer of a pressure-sensitive adhesive is particularly advantageously used. When the feminine hygienic pad is used, the pad can be attached to a desired position of the fabric of an underwear after the release film has been removed.

As the backing sheet of the composite absorption sheet used in the present invention, a sheet made of a conventional material and having a conventional shape can be used.

The backing sheet of the composite absorption sheet used in the present invention plays the role of a base sheet which fixes or contains the sheet of fluid-absorbing material. The backing sheet may be a sheet separate from the sheet of a fluid-absorbing material or a sheet integrally formed with the sheet of a fluid-absorbing material.

It is necessary that the backing sheet be made of a material which does not allow permeation of the fluid absorbed into the sheet of a fluid-absorbing material further to the other side of the backing sheet. Examples of the backing sheet include thin films of a resin, paper sheets and non-woven fabrics laminated with an ultra-thin film of a resin, and paper sheets and non-woven fabrics treated for water repellence. Paper sheets and non-woven fabrics have the advantage that the materials form a slurry in water and can be washed away when the pad is disposed in a flush toilet.

It is necessary that the backing sheet of the lowest composite absorption sheet which constitutes the bottom layer of the multi-layer feminine hygienic pad of the present invention have a mechanism for fixing the backing sheet to a desired position of the fabric of an underwear.

As the above mechanism, a mechanism used in conventional feminine hygienic pads can be used without particular restriction. For example, a layer of a pressure-sensitive adhesive is formed at the whole part, the central part, or a peripheral part of the lowest backing sheet and the pad is fixed to a desired position of an underwear with the layer of the pressure-sensitive adhesive. A release film is attached to the surface of the layer of a pressure-sensitive adhesive until the pad is used, and the pad can be fixed exactly to the desired position of the underwear when the release film is removed before use.

The composite absorption sheets of the present invention may be made of the same material and may have the same dimension. Alternatively, the composite absorption sheets may be made of different materials and may have different dimensions and thicknesses. When the materials and dimensions are different, the amount of absorption can suitably be adjusted in accordance with the time. Moreover, when the sheets of a fluid-absorbing material or backing sheets have each a color different from others in a pad having several composite absorption sheets laminated together, the pad is convenient for use because the number of the remaining composite absorption sheet can be found by the color of the sheets.

The backing sheets in the upper composite absorption sheets in the present invention play the same role and are made of the same material as those of the backing sheet of the lowest composite absorption sheet except that the lower surface of the backing sheet is required to have a mechanism for temporarily attaching the backing sheet to a desired part of the lower composite absorption sheet or directly to the fabric of an underwear in place of the mechanism for fixing the backing sheet to the fabric of an underwear.

The present invention is described in more detail with reference to figures of examples in the following.

In the following examples, the laminate structures contain 2 to 5 layers. However, the present invention is not limited to this laminate structure but includes any embodiments having two or more layers.

FIG. 1 shows an embodiment of the feminine hygienic pad of the present invention having a structure in which the lowest composite absorption sheet 1 is composed of a sheet of a fluid-absorbing material 10 made of a water-absorbing macromolecular compound and a backing sheet made of a thermoplastic resin film 11 having a larger dimension by area than that of the sheet 10, and an upper composite absorption sheet 2 is laminated to the lowest composite absorption sheet 1 in such a manner that the upper composite absorption sheet 2 can be detached from the lowest composite absorption sheet 1.

To the lower side of the sheet of a fluid-absorbing material 10, a backing sheet 11 having a larger dimension by area than that of the sheet 10 is attached. On the sheet of a fluid-absorbing material 10, a face film 12 (a porous film) which is made of a thermoplastic resin and allows permeation of fluid is laminated. The backing sheet 11 and the face film 12 are attached together at the peripheral parts. Thus, the sheet of a fluid-absorbing material 10 is contained between the backing sheet 11 and the face film 12, and the lowest composite absorption sheet 1 is formed. The upper composite absorption sheet 2 is a laminate having the same structure as that of the lowest composite absorption sheet 1 and composed of a sheet of a fluid-absorbing material 20, a backing sheet 21, and a face film 22.

In the embodiment shown in FIG. 1, the whole lower side of the backing sheet 11 is coated with a layer of a pressure-sensitive adhesive A, and a release film B is attached to the layer of the adhesive A. The layer of a pressure-sensitive adhesive A coating the lower side of the backing sheet 11 is a layer of a pressure-sensitive adhesive used in conventional feminine hygienic pads and used for fixing the backing sheet 11 to a desired position of an underwear after removing the release film B.

In FIG. 1, the backing sheets 11 and 12, the face films 12 and 22, the layer of a pressure-sensitive adhesive A, and the release film B are each shown by a single line for simplicity. The sheets of a fluid-absorbing material 10 and 20 are each shown by a bold line. In the following figures, a bold line showing a sheet of a fluid-absorbing material contained in a composite absorption sheet is occasionally omitted to avoid complicated illustration.

The mechanism of fixing the lowest backing sheet 11 by using a release film has been used in conventional feminine hygienic pads. When the backing sheet is attached to a desired position of an underwear with a layer of a pressure-sensitive adhesive, the layer of a pressure-sensitive adhesive exposed after removal of the release film tends to stick to various places. When a conventional feminine hygienic pad is used while staying outside the home, this causes drawbacks in that a difficult and careful handling is required to fix the pad to an exact position of an underwear in a small space of a toilet while the underwear is put on and naturally it takes a long time, and in that a relative loud sound is made when the backing sheet of a used pad is peeled off from the underwear.

When the feminine hygienic pad of the present invention is used, the pad can be fixed at home to an exact position of an underwear before the underwear is put on, and a used sheet can be replaced with a fresh sheet in a short time because the replacement requires peeling off the uppermost composite absorption sheet alone while the backing sheet of the lowest composite absorption sheet remains fixed to the original position. In other words, fixing the feminine hygienic pad of the present invention itself takes the same time as that required for fixing a conventional feminine hygienic pad. However, the fixing is generally made at home when the time for the fixing is not limited and causes no problem. The feminine hygienic pad of the present invention has the advantage that the time required for the replacement which is the cause of trouble while staying outside the home can be decreased to a great extent.

Figure 2A:
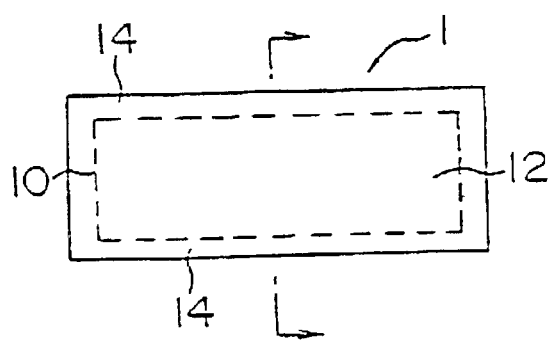
FIGS. 2(a) and 2(b) show a plan view and a transverse sectional view cut along the line indicated by the arrows in FIG. 2(a), respectively, of the composite absorption sheet at the lowest layer in the multi-layer feminine hygienic pad shown in FIG. 1.
Figure 2B:
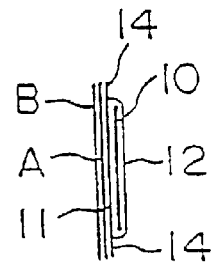

FIG. 2 is also related to the above embodiment of the present invention. FIGS. 2(a) and 2(b) show a plan view and a sectional view cut along the line indicated by the arrows in FIG. 2(a), respectively, of the lowest composite absorption sheet comprising the backing sheet 11 in the multi-layer feminine hygienic pad shown in FIG. 1. The backing sheet 11 is formed to such a shape that the peripheral part 14 is extended from the peripheral line (shown by the dotted line) of the sheet of a fluid-absorbing material 10.

Figure 3A:
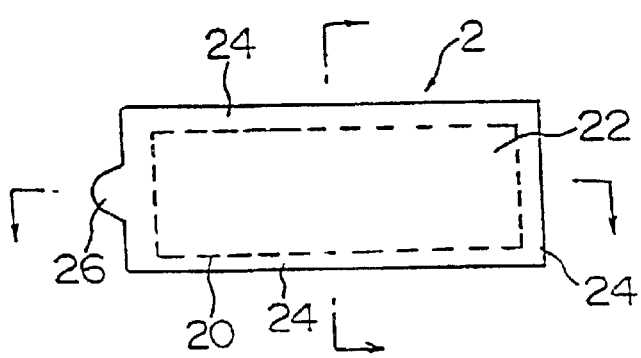
FIGS. 3(a), 3(b), and 3(c) show a plan view, a longitudinal sectional view cut along the line indicated by the horizontal arrows in FIG. 3(a), and a transverse sectional view cut along the line indicated by the vertical arrows in FIG. 3(a), respectively, of the composite absorption sheet at the uppermost layer of the multi-layer feminine hygienic pad shown in FIG. 1.
Figure 3C:
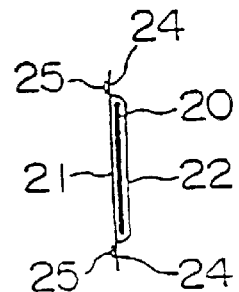
Figure 3B:
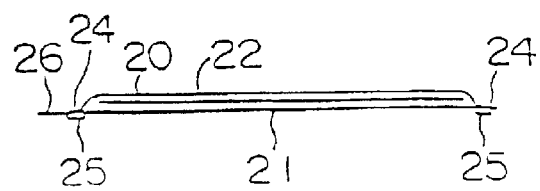

FIGS. 3(a), 3(b), and 3(c) show the upper composite absorption sheet in the multi-layer feminine hygienic pad shown in FIG. 1. The lower side of the peripheral part 24 of the backing sheet 21 in the upper composite absorption sheet 2 is coated with a layer of a pressure-sensitive adhesive 25.

The lower side of the backing sheet 21 of the upper composite absorption sheet 2 shown in FIGS. 3(a), 3(b), and 3(c) is placed on the lowest composite absorption sheet 1 shown in FIGS. 2(a) and 2(b), and the upper side of the peripheral part of the backing sheet 11 in the lower composite absorption sheet and the lower side of the peripheral part of the backing sheet 21 in the upper composite absorption sheet are attached together with the layer of a pressure-sensitive adhesive 25 disposed between the peripheral parts. Thus, the embodiment of the feminine hygienic pad having the sectional structure shown in FIG. 1 is formed.

In this embodiment of the present invention, the sheet of a fluid-absorbing material 10 is contained between the backing sheet 11 and the backing sheet 21 and does not absorb moisture in the atmosphere while the pad is attached to an underwear. However, this contained structure is not the essential part of the present invention. A portion of the peripheral part 24 may be left without being coated with the layer of an adhesive 25 so that fingers can be inserted from this peripheral part not coated with the layer of an adhesive, and the upper composite absorption sheet 2 can easily be peeled off.

A protruded tongue 26 may also be formed at a peripheral part of the backing sheet of the upper absorbing sheet and/or the backing sheet of the lowest composite absorption sheet to facilitate peeling off the backing sheet of the uppermost composite absorption sheet, for example, in such a manner shown in FIGS. 3(a) and 3(b). When the protruded tongues in the upper backing sheet and the lowest backing sheet are formed at positions close to each other, the peeling off can be made more easily.

When this embodiment of the feminine hygienic pad having the upper composite absorption sheet is fixed to an underwear after the release film B is peeled off, the upper composite absorption sheet 2 exposed at the upper surface absorbs fluid. When the uppermost composite absorption sheet 2 is replaced with a fresh composite absorption sheet in a toilet, the used composite absorption sheet can be peeled off by pulling the protruded tongue 26 in the backing sheet 21 from the peripheral part of the backing sheet 11. The handling for the pulling off can be conducted while the backing sheet 11 is fixed to the underwear.

When the feminine hygienic pad of the present invention comprises three or more composite absorption sheets, peeling off unused internal composite absorbing sheets together with the used composite absorption sheet by mistake can be prevented by forming a protruded tongue having a similar shape (not shown in the figures) in the backing sheet of each composite absorption sheet between the uppermost composite absorption sheet and the lowest composite absorption sheet at a position close to the position of the tongue 26 in the backing sheet of the uppermost composite absorption sheet.

When the backing sheet 21 is peeled off, the layer of a pressure-sensitive adhesive 25 at the peripheral part is attached to the lower surface of the backing sheet 21 and peeled off together. No layer of the pressure-sensitive adhesive is transferred to the upper surface of the backing sheet 11, and trouble caused by the attachment of the adhesive to the skin or the hair can be avoided.

The above phenomenon arises from the general principle that a pressure-sensitive adhesive remains attached to the originally coated surface. In view of this phenomenon, it is preferred that the layer of a pressure-sensitive adhesive 25 at the peripheral part is applied to the peripheral part of the lower side of the backing sheet 21. When the peripheral part of the upper side of the backing sheet 11 of the lowest composite absorption sheet is coated with a releasing agent, the transfer of the adhesive can completely be prevented. By coating the surface of the lower backing sheet with a releasing agent in this manner, the layer of the pressure-sensitive adhesive is transferred to the upper backing sheet and removed from the lower backing sheet after the upper composite absorption sheet is removed even when the surface of the lower backing sheet is coated with a pressure-sensitive adhesive. A pressure-sensitive adhesive of the micro-balloon type which has a small adhesive strength and shows no transfer, such as adhesives used in labels, can also be used advantageously in the present invention.

In the present invention, when the composite absorption sheets are attached together not by temporary attachment at the peripheral part of the composite absorption sheets but by temporary attachment of the whole surface of the lamination between the composite absorption sheets, a pressure-sensitive adhesive having a small adhesive strength and showing no transfer of the adhesive can be used. When a porous cover film is disposed on the sheet of a fluid-absorbing material of the feminine hygienic pad, the composite absorption sheets can be laminated together by temporary attachment between the whole lower surface of the upper composite absorption sheet and the porous cover film in the lower composite absorption sheet in addition to the temporary attachment between the peripheral parts of the composite absorption sheets. When the composite absorption sheets are temporarily attached together by attachment between the whole surfaces of the upper sheet and the lower sheet in addition to the attachment between the peripheral parts, using a pressure-sensitive adhesive having an ordinary adhesive strength causes an excessively strong adhesion and also the possibility that the adhesive is transferred to pores of the cover film.

The pressure-sensitive adhesive having a small adhesive strength can be obtained by decreasing the concentration of the adhesive macromolecular compound dissolved in a solvent when an ordinary pressure-sensitive adhesive is used. The pressure-sensitive adhesive having a small adhesive strength can also be obtained by using a substance having an essentially small adhesive strength, such as a pressure-sensitive adhesive of the micro-balloon type having a small adhesive strength. The pressure-sensitive adhesive having a small adhesive strength used in the present invention is a pressure-sensitive adhesive having an adhesive strength of 60% or less, preferably 40% or less, of that of the ordinary pressure-sensitive adhesive, more specifically, a pressure-sensitive adhesive having an adhesive strength of 10 to 500 gf/20 mm, preferably 20 to 200 gf/200 mm, at the temperature of 20° C. when the adhesive is applied to a film of a flexible resin and the adhesive strength is measured by the T-peeling test.

Figure 4A:
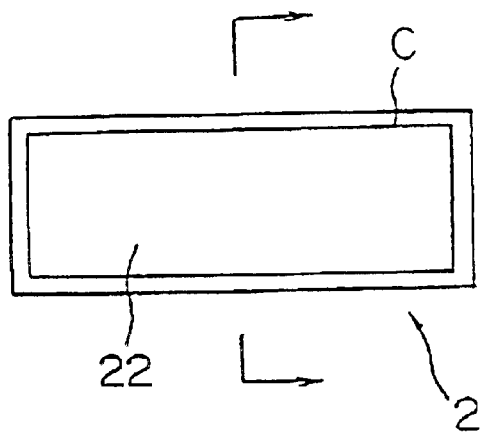
FIGS. 4(a) and 4(b) show a plan view and a transverse sectional view cut along the line indicated by the arrows in FIG. 4(a), respectively, of a multi-layer feminine hygienic pad as another embodiment of the present invention.

In another embodiment of the temporary attachment in the present invention, layers in the laminate are temporarily attached together by intermediate melt adhesion of thee peripheral parts of a upper backing sheet 21 made of a film of a thermoplastic resin and a lower backing sheet 11 made of a film of a thermoplastic resin at a heat sealed part C as shown in the plan view of FIG. 4(a).

In the above embodiment, when the upper and lower backing sheets are simply melt adhered at the heat sealed part C, the two backing sheets cannot be peeled off to separate them unless two sheets are broken.

Figure 4B:
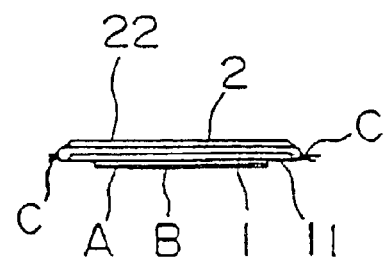

In the embodiment of the present invention shown in FIGS. 4(a) and 4(b), the lower side of the upper backing sheet 21 or the upper side of the lower backing sheet 11 is coated with a layer of an oil ink as the agent for preventing heat sealing.

The technology using the temporary attachment by intermediate melt adhesion in the heat sealing or the heat sealing with melt cutting has generally been known and is occasionally used in the process for producing a bag by using a film of a thermoplastic resin. A conventional agent for preventing heat sealing used in the intermediate melt adhesion in the above technology can be used also in the present invention without any restriction. Any agents which can prevent melt adhesion in heat sealing, such as printing ink compositions, oil compositions containing the same components as those of printing ink compositions excluding coloring pigments, paraffins, oils and fats, low molecular weight amorphous polypropylene, pressure-sensitive adhesives, and heat-sensitive adhesives, can advantageously be used without any restriction.

When a thermoplastic film is coated with an agent for preventing melt adhesion, and the heat sealed part C is formed between the thermoplastic film and another thermoplastic film in the presence of a layer of the agent for prevention of melt adhesion disposed between the two thermoplastic films, an intermediate melt adhesion is formed at the heat sealed part of the two films. When the two film are attached by the intermediate melt adhesion, the two films are peeled off by rubbing with fingers. When the two attached sheets are separated at an end of the laminate, the backing sheet 21 can easily be peeled off from this separated part. Therefore, in the embodiment shown in FIGS. 4(a) and 4(b), the upper backing sheet 21 can easily be peeled and removed by pulling apart the ends of the lowest backing sheet 11 and the upper backing sheet 21 which are at the outside of the heat sealing C and not attached together. It is also convenient for peeling in this case that a tongue is formed at the peripheral part. When the peripheral part of the upper backing sheet 21 is made larger, the flexible backing sheet 21 alone can be peeled off more easily. In the laminate structure having three or more composite absorption sheets, when a tongue is formed in each composite absorption sheet in such as manner that an upper composite absorption sheet has a longer tongue than a lower composite absorption sheet, the uppermost composite absorption sheet alone can surely be removed by pulling the longest remaining tongue.

The uppermost composite absorption sheet can easily be peeled off while the pad is fixed to an underwear when this embodiment of the feminine hygienic pad of the present invention is used. The transfer of an adhesive is entirely absent because no pressure-sensitive adhesive is used. The surface formed by the peeling is dry, and the pad can be used comfortably.

In the embodiment shown in FIGS. 4(a) and 4(b), the peripheral parts can also be melt cut by a heated blade in place of forming heat sealed part C in the presence of an agent for preventing melt adhesion disposed between the sheets. In this case, the ends of the lowest backing sheet 11 and the upper backing sheet 21 are intermediately melt adhered, and the parts outside the intermediately melt adhered end line are removed. Therefore, the handling for the peeling is more difficult because peripheral parts which are not attached together are not remaining at the outside unlike the product formed by the heat sealing. However, this structure provides more stability of the product because there is no possibility that the backing sheet 21 is peeled off during use. A suitable structure can be selected from these structure in accordance with the requirements. When the sheets are attached together by the melt cutting, it is preferred that a corner of the part attached by the melt cutting is mechanically cut off. The backing sheet 21 can be peeled off by inserting fingers through the unattached corner formed by the cutting.

As another embodiment of the present invention, it is also advantageous that a heat-sensitive adhesive is applied to one of the lower side of the upper backing sheet 11 and the upper side of the lower backing sheet 21, preferably to the whole lower side of the upper backing sheet 21, and then the peripheral parts of the sheets are attached together by heat pressing. In this case, the heat-sensitive adhesive applied to the sheet is dry and does not have the stickiness at all. The adhesive exhibits the adhesive property by melting when it is pressed under heating. This adhesive is convenient because the adhesive remains dry after the sheets are peeled off and does not show any stickiness. Because the adhesion by heat pressing is conducted on the peripheral parts, the heat is rapidly transferred and the heat pressing can easily be made.

A heat-sensitive adhesive can be applied to the whole lower surface of the upper backing sheet, and the difficulty in a pressure-sensitive adhesive that the peripheral part must selectively be coated can be avoided. Thus, the heat-sensitive adhesive is conveniently used in the production of the pad.

Figure 5A:
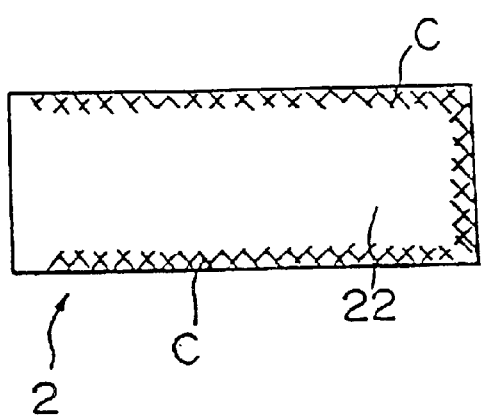
FIGS. 5(a), 5(b), and 5(c) show three types of multi-layer feminine hygienic pad as other embodiments of the present invention.
Figure 5B:
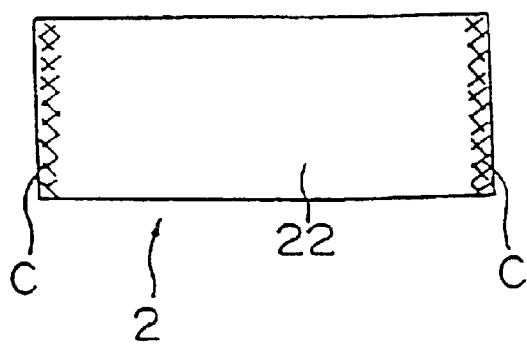
Figure 5C:
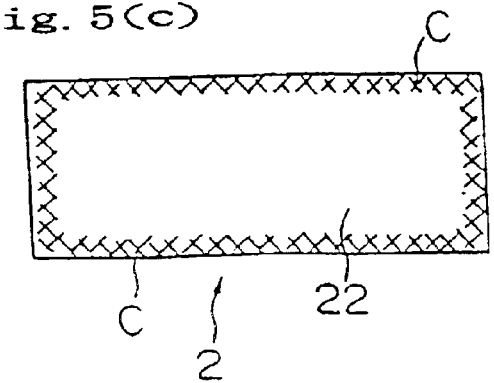

The heat-sensitive adhesive which coats the whole lower surface is dry at an ambient temperature and is not sticky. Therefore, a heat sealed part C can be formed at a desired part, for example along the whole peripheral part as shown in FIG. 5(c), along three edges as shown in FIG. 5(a), or along two edges as shown in FIG. 5(b), by pressing the necessary part alone. This method of temporary attachment is particularly advantageous for laminating three or more composite absorption sheets because the process for the temporary attachment is simple.

In the case shown in FIG. 5(a), it is preferred that the length of extension of the open edge of an upper backing sheet is made successively longer than that of the backing sheet disposed directly below. In the case shown in FIG. 5(b), it is preferred that the lengths of extension of the opposite open edges of an upper backing sheet are made successively longer than those of the backing sheet disposed directly below. In the case shown in FIG. 5(c), it is preferred that the lengths of extension of any edges or all edges of an upper backing sheet is made successively longer than those of the backing sheet disposed directly below.

In the above cases, even when the layer of a heat-sensitive adhesive is left remaining on the surface of the lowest backing sheet 11, the problem that the adhesive sticks to the skin does not arise.

Taking advantage of the above property of the heat-sensitive adhesive, the whole lower side of the upper composite absorption sheet can be coated with a heat-sensitive adhesive, and the upper composite absorption sheet can be attached to the face film of the lower composite absorption sheet not only at the peripheral part but also at the whole surface.

In the heat pressing step in the process for producing the multi-layer feminine hygienic pad of the present invention, a backing sheet of an upper composite absorption sheet is attached to a porous face film of a lower composite absorption sheet by heat pressing to prepare a laminate sheet. A plurality of this laminate sheets are prepared in advance. Sheets of a fluid-absorbing material are inserted between the plurality of the prepared laminate sheets, and then the multi-layer feminine hygienic pads can efficiently be produced.

When the above laminate sheet is not prepared by heat pressing in advance, the sheets of a fluid-absorbing material insulate the heat for the heat pressing, and the heat pressing cannot be made at the whole surfaces of the composite absorption sheets.

When the whole surface is temporarily attached together by coating the whole lower surface of the upper composite absorption sheet with a pressure-sensitive adhesive having a small adhesive strength or with a heat-sensitive adhesive as described above, the process for production can be made easier than the process in which the peripheral part alone is coated. The temporary attachment at the whole surfaces of the composite absorption sheets with a pressure-sensitive adhesive having a small adhesive strength or with a heat-sensitive adhesive is suitably used in combination with other methods of temporary attachment of the present invention. Particularly, this process can be used in combination with the methods of temporary attachment by using a pressure-sensitive adhesive at the peripheral part described in (2), by using an agent for preventing melt adhesion described in (5), by using heat pressing described in (7), by using perforation described in (8), and by using perforation inside the heat sealed part described in (10), and with the method of temporary attachment at the peripheral part by forming protrusions and depressions which is described in (12).

Figure 6A:
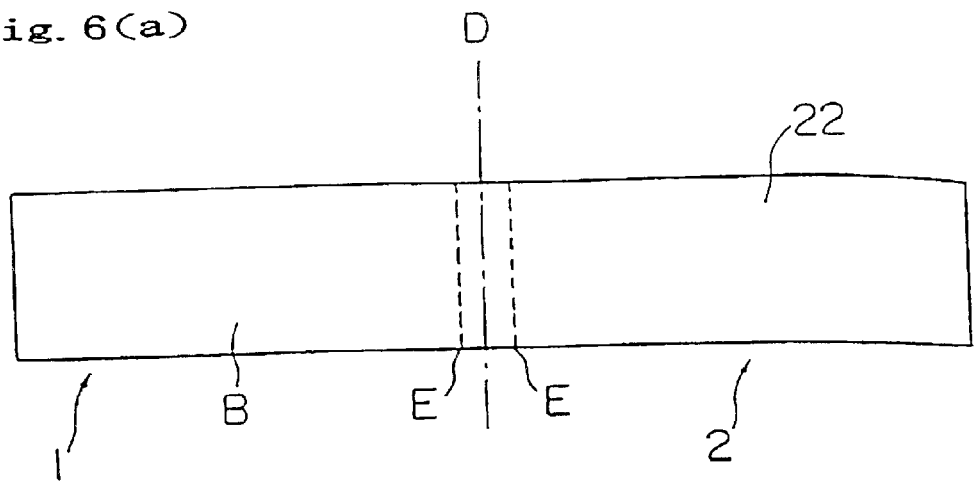
FIGS. 6(a) and 6(b) show a plan view and a longitudinal sectional view, respectively, of the feminine hygienic pad shown in FIG. 6(c) in the developed condition.
Figure 6B:
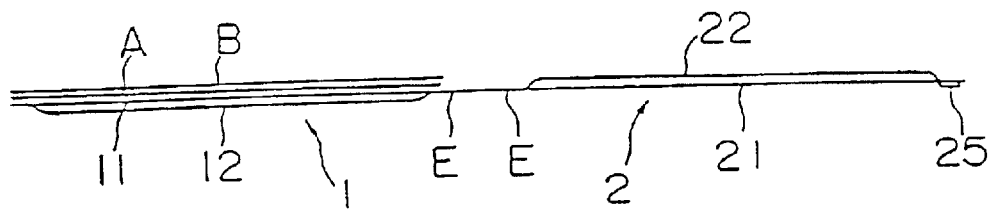
Figure 6C:
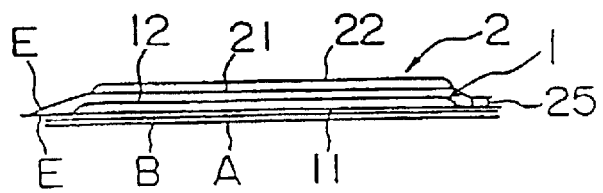
FIG. 6(c) shows a longitudinal sectional view of a multi-layer feminine hygienic pad of a multi-layer feminine hygienic pad as another embodiment of the present invention.
Figure 6D:
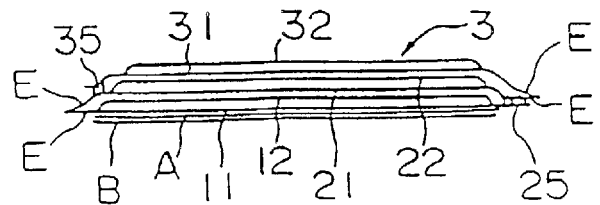
FIG. 6(d) shows a longitudinal sectional view of a multi-layer feminine hygienic pad which is similar to the pad shown in FIG. 6(c) and has three layers.
Figure 7A:
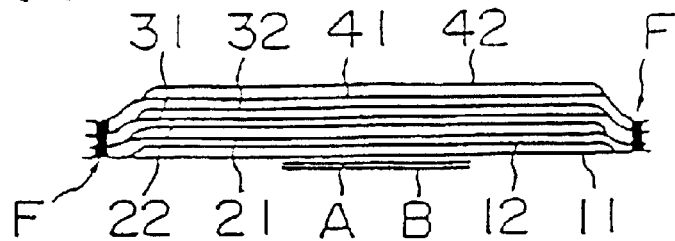
FIGS. 7(a), 7(b), and 7(c) show a transverse sectional view, a longitudinal sectional view, and a bottom view, respectively, of a multi-layer feminine hygienic pad as another embodiment of the present invention.
Figure 7B:
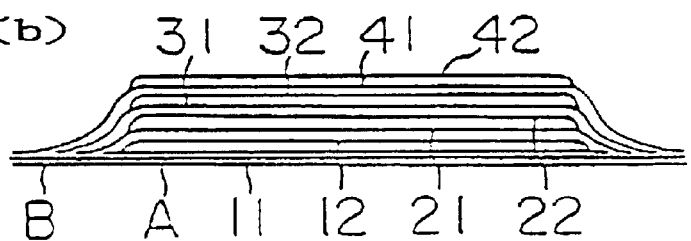
Figure 7C:
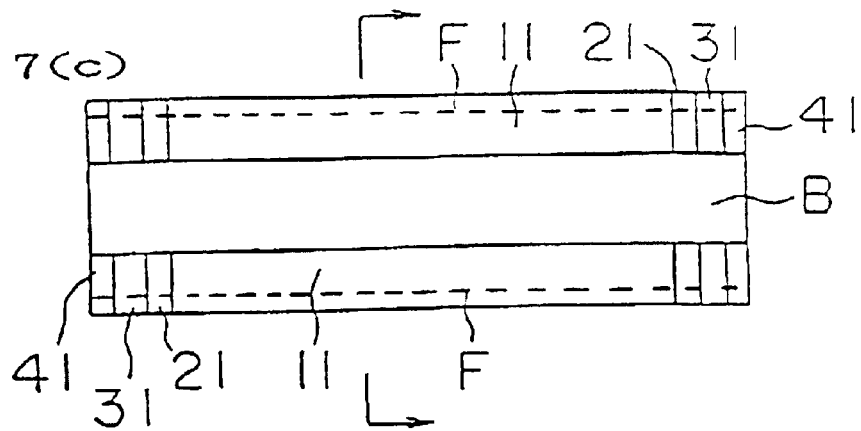
Figure 7D:
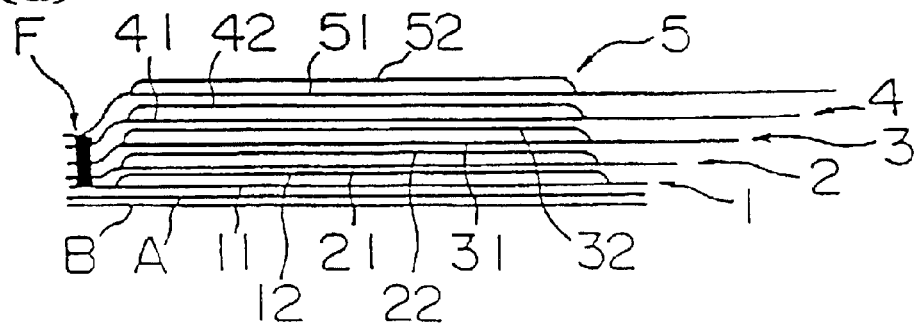
FIG. 7(d) shows a longitudinal sectional view of a multi-layer feminine hygienic pad as still another embodiment of the present invention.

In another embodiment of the present invention, a laminate structure contains a folded sheet to form two composite absorption sheet as shown in FIG. 6(c). As shown in FIGS. 6(a) and 6(b) which show the plan view and the sectional view, respectively, of the folded sheet in the unfolded condition, the lowest composite absorption sheet 1 is composed of a backing sheet 11, a sheet of a fluid-absorbing material 10 (not shown in the figures), and a face film 12. An upper composite absorption sheet 2 is composed of a backing sheet 21, a sheet of a fluid-absorbing material 20 (not shown in the figures), and a face film 22. Two perforation lines E are formed at both sides of the boundary line D.

When the composite absorption sheet 1 is brought under the composite absorption sheet 2 both shown in FIGS. 6(*a*) and 6(*b*) by folding the sheet common to both composite absorption sheets at the boundary line D, the laminate structure having the sectional structure shown in FIG. 6(*c*) can be obtained. When the sheet in the laminate is torn by pulling at the boundary line D by fingers, the composite absorption sheet 1 can be separated from the composite absorption sheet 2 at the two perforation lines E.

In the embodiment shown in FIGS. 6(*a*) to 6(*d*), the lower side of the peripheral part of the composite absorption sheet 2 opposite to the folded boundary line is temporarily attached to the corresponding peripheral part of the composite absorption sheet 1 with a layer of a pressure-sensitive adhesive 25. Shift of the relative position of the layers in the laminate structure during transportation and use is prevented by this temporary attachment.

The perforation E is formed in two parallel lines. When an end of the part between the two perforation lines is picked and tore off, the part is separated from the laminate structure, leaving the laminate structure unchanged. Thus, the upper and lower composite sheets in the laminate structure are easily separated at one edge. When the used composite absorption sheet is peeled by pulling upwards by holding the above-separated edge, the opposite edges temporarily attached with the layer of a pressure-sensitive adhesive 25 can easily be separated.

FIGS. 6(*a*) to 6(*d*) show the embodiment having two composite absorption sheets. This folded structure can particularly advantageously be applied to multi-layer feminine hygienic pads having 3 or more composite absorption sheets, such as the pad shown in FIG. 6(*d*).

In the embodiment of the present invention shown in FIGS. 7(*a*) to 7(*d*), the temporary attachment is conducted by mechanical pressing.

As the mechanical pressing used in this embodiment, the conventional high pressure pressing, such as the pressing used for preparation of laminated post cards, the ordinary high pressure pressing in combination with a treatment which provides a slightly adhesive property to the faced surfaces inside the sheets, or the pressing by press surfaces having protrusions and depressions to form depressions and protrusions on the pressed surfaces, followed by temporary attachment of the pressed surfaces by fitting the protrusions and depressions to each other, can be used.

The temporary attachment by the mechanical pressing is effective when the material of a backing sheet of a composite absorption sheet is a firm material, such as paper or synthetic paper.

In FIGS. 7(*a*) to 7(*d*), both side edges of the composite absorption sheets are temporarily attached together by the mechanical pressed parts F. FIG. 7(*a*) shows a longitudinal sectional view, and FIG. 7(*b*) shows a transverse sectional view. FIG. 7(*c*) shows a bottom view. The central part of the bottom surface is protected with a release film, and the surface to which the release film is attached is coated with a layer of a pressure-sensitive adhesive. Peripheral parts of upper composite absorption sheets 21, 31, and 41 are each extended from the corresponding peripheral part of the composite absorption sheet disposed directly below, and a pressure-sensitive adhesive is applied to the extended part. The layers of the pressure-sensitive adhesive are all attached to a single release film B.

The coating of the pressure-sensitive adhesive to the backing sheet can be conducted in accordance with a conventional method, in which the pressure-sensitive adhesive is applied to the release film in the first step, and then the coated release film is attached to the laminate shown in FIG. 7(*c*) to transfer the pressure-sensitive adhesive to the backing sheets in the laminate.

FIG. 7(*d*) shows a sectional view of an embodiment in which composite absorption sheets 1, 2, 3, 4, and 5 are laminated together, one edge or three edges of the backing sheets are temporarily attached together by mechanical pressing, and the edges 51, 41, 31, 21, and 11 of the backing sheets which are not temporarily attached together are extended in such a manner that an upper edge is extended from a lower edge, successively.

Figure 8A:
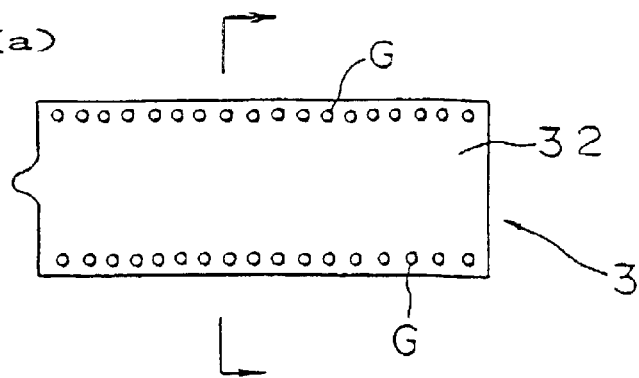
FIGS. 8(a) and 8(b) show a plan view and a transverse sectional view, respectively, of a multi-layer feminine hygienic pad as another embodiment of the present invention.
Figure 8B:
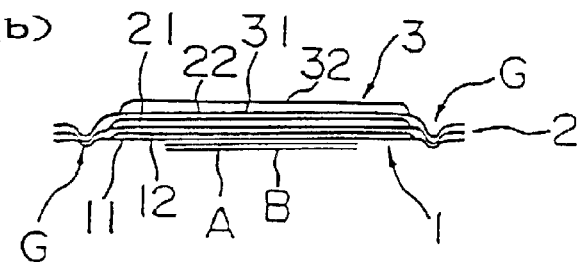

In FIGS. 8(*a*) and 8(*b*), the opposite peripheral parts of composite absorption sheets are pressed together at the position of a row of depressions G and temporarily attached together by using the row of depressions. The laminate can be temporarily attached together by pressing by a press having a corresponding row of protrusions. This method is particularly effective when the material of the backing sheet is a firm material, such as paper. In place of the row of depressions, troughs and furrows can also be used effectively.

In the embodiment shown in FIGS. 9(*a*) and 9(*b*), the lower side of a backing sheet of an upper composite absorption sheet is temporarily attached not to the lowest composite absorption sheet but directly to an underwear.

In the embodiment shown in FIGS. 9(*a*) and 9(*b*), the temporary attachment of two layers by using perforations is used additionally. The backing sheet of an upper composite absorption sheet 2 has a large extended part at both longitudinal edges to form extended tongues 27 and 28. On the lower side (on the upper side in FIG. 9(*a*)) of the extended tongues 27 and 28, a layer of a pressure-sensitive adhesive A is formed. A layer of a pressure-sensitive adhesive is formed also on the whole lower side of the lowest composite absorption sheet 1. The release film B attached to the lower side of the lowest composite absorption sheet 1 also has extended tongues m and n which have the shape corresponding to that of the extended tongues 27 and 28 in the upper composite absorption sheet and are extended from the longitudinal edges of the lowest composite absorption sheet.

When a laminate is prepared from the components having the above structure, the extended tongues 27 and 28 of the upper composite absorption sheet in the prepared laminate can directly be attached to the fabric of an underwear as shown in FIG. 9(*b*).

In this embodiment of the feminine hygienic pad, the pad has the structure formed by folding the structure shown in the figures, and a single sheet of the release film is attached to cover the whole layers of a pressure-sensitive adhesive on the lower sides of the extended tongues 27 and 28 and on the lower side of the backing sheet 11 before the pad is used. Therefore, there is no possibility that shift of the relative position of the composite absorption sheet 1 and the composite absorption sheet 2 takes place during storage. When the pad is used, the release film is peeled off, and the composite absorption sheet 1 and the composite absorption sheet 2 are fixed to a desired position of an underwear with the layer of a pressure-sensitive adhesive on the lower side of the backing sheet 11 and the layers of a pressure-sensitive adhesive on the lower sides of the extended tongues 27 and 28, respectively. The composite absorption sheet 2 is temporarily attached to the lowest composite absorption sheet 1 at the boundary line D of the folding, and the longitudinal edges of the composite absorption sheet are fixed to the fabric of an underwear with the layers of a pressure-sensitive adhesive at the lower sides of the extended tongues 27 and 28.

To replace the used composite absorption sheet with a fresh composite absorption sheet, the part between the two perforation lines is pulled to cut the sheet into the upper and lower parts, and the used composite absorption sheet is removed by pulling the end formed by the cutting. The parts of the extended tongues 27 and 28 fixed to the underwear with the layers of a pressure-sensitive adhesive can easily be peeled off by this handling.

Figure 9A:
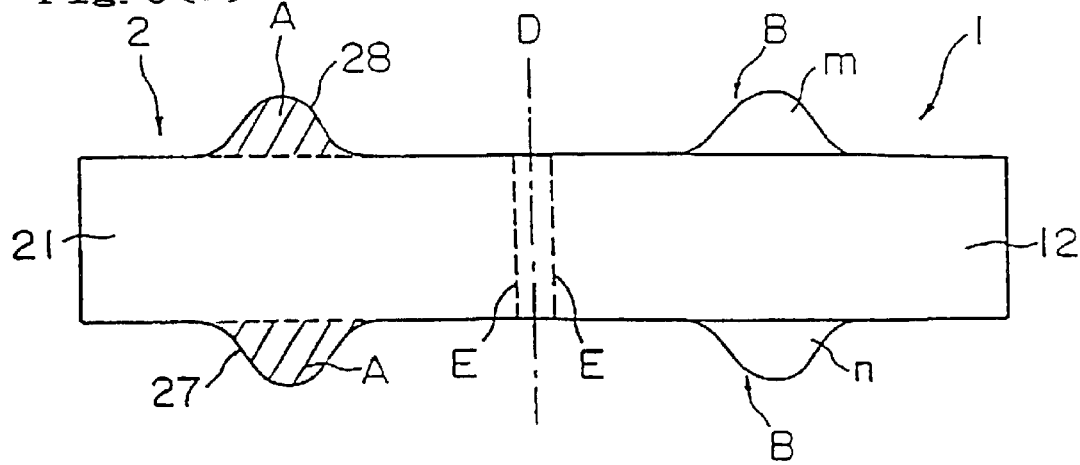
FIG. 9(a) shows a plan view of the multi-layer feminine hygienic pad shown in FIG. 9(b) in the developed condition.
Figure 9B:
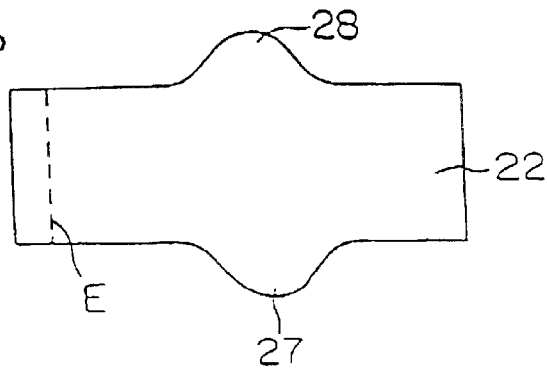
FIG. 9(b) shows a plan view of a multi-layer feminine hygienic pad as another embodiment of the present invention.
Figure 10A:
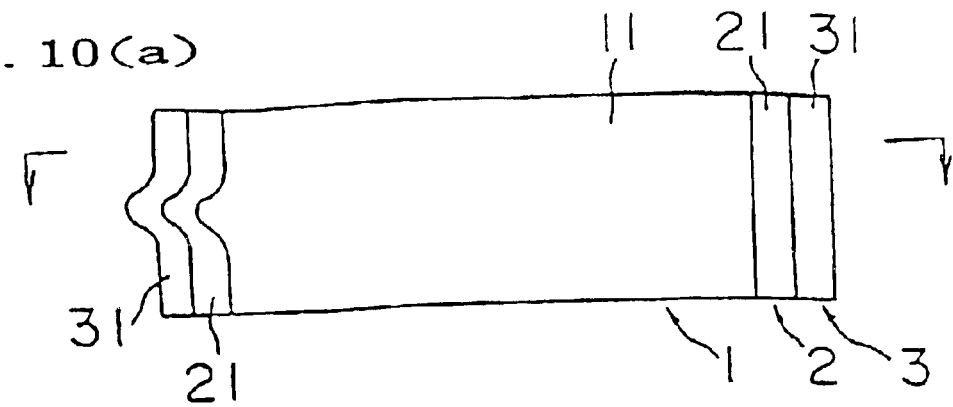
FIGS. 10(a), 10(b), and 10(c) show a bottom view, a longitudinal sectional view, and expanded partial sectional view showing the sectional structure, respectively, of a multi-layer feminine hygienic pad as another embodiment of the present invention.
Figure 10B:
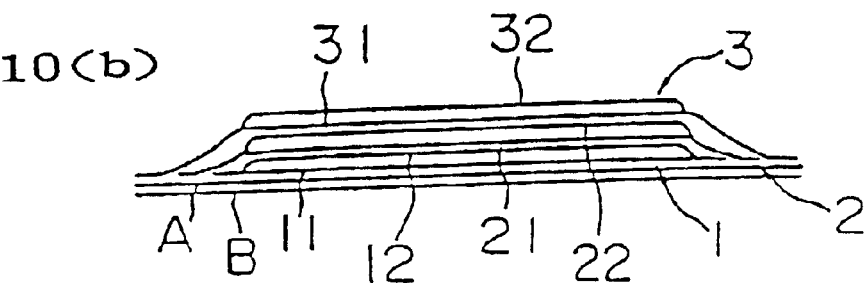
Figure 10C:
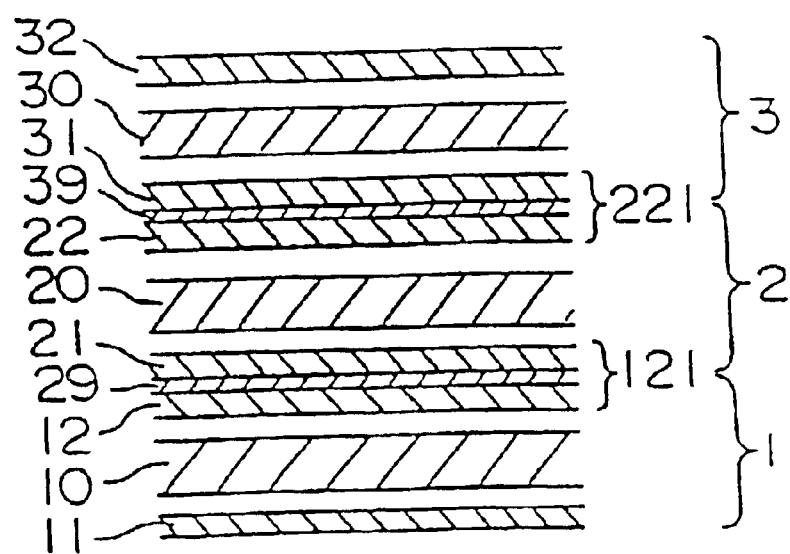

FIGS. 10(a) to 10(c) show an embodiment which is obtained by further development of the embodiment shown in FIGS. 9(a) and 9(b). In this embodiment, two or more composite absorption sheets are laminated together. Shorter edges of an upper backing sheet 21 and 31 are each extended from the shorter edges of the backing sheet disposed below.

Layers of a pressure-sensitive adhesive are formed on the lower side of the lowest backing sheet in the laminate structure and on the lower sides of the parts of the backing sheets of the upper composite absorption sheets extended each from the composite absorption sheet disposed below. The whole layers of a pressure-sensitive adhesive are covered with a single common sheet of a release film B to fix the laminate structure. FIG. 10(a) shows a bottom view in which the release film B is removed. This embodiment of the multi-layer feminine hygienic pad has the possibility that the pad is decomposed to the component sheets as soon as the release film is removed. Therefore, it is preferred that the above-described temporary attachments used in the laminate structures of the present invention comprising the composite absorption sheets are used in combination. Particularly, by coating the whole part of the lower sides of the backing sheets 31 and 21 of the upper composite absorption sheets with the layers 39 and 29, respectively, of a pressure-sensitive adhesive having a small adhesive strength as shown in the expanded view of FIG. 10(c), the backing sheets 31 and 21 can temporarily be attached to the face films 22 and 12, respectively, of the composite absorption sheets disposed below. A heat-sensitive adhesive may be used in place of the pressure-sensitive adhesive having a small adhesive strength.

The multi-layer feminine hygienic pads of the present invention in which the whole surface of a composite absorption sheet is attached to another composite absorption sheet to form a laminate with a pressure-sensitive adhesive having a small adhesive strength or a heat-sensitive adhesive are all efficiently produced in accordance with the following process.

Films of a thermoplastic resin are used as the backing sheet and the face film. In the expanded laminate structure shown in FIG. 10(c), a face film 12 and a backing film 21 both in the form of a continuous long sheet are attached together by an adhesive to prepare a single long laminate sheet 121 having two layers (3 layers including the layer of an adhesive are shown in the figure). Separately in the same manner, a face film 22 and a backing sheet 31 are attached together with an adhesive to prepare a long laminate sheet 221. A lowest backing sheet 1 and a face film 32 both in the form of a continuous long sheet are also prepared separately.

Sheets of a fluid-absorbing material 10, 20, and 30 each in a plurality of pieces are disposed and fixed on the lowest backing sheet 11, the laminate sheet 121, and the laminate sheet 221, respectively, at positions separated by a prescribed distance to the longitudinal direction of the long sheets. The order of the sheets may be reversed so that sheets of a fluid-absorbing material 10, 20, and 30 are disposed and fixed below the laminate sheet 121, the laminate sheet 221, and a surface sheet 32, respectively, at positions separated by a prescribed distance to the longitudinal direction of the long sheets.

The lowest backing sheet 11, the laminate sheet 121, and the laminate sheet 221 are continuously laminated together in such a manner that the sheets of a fluid-absorbing material fixed on the three long sheets are disposed at the same position to the longitudinal direction. The face film 32 is laminated to the obtained laminate to prepare a long laminate sheet having 4 layers.

The prepared long laminate sheet having 4 layers is fed to a heat pressing table by a one-pitch movement. The space around the sheet of a fluid-absorbing material is intermittently pressed by a heated press or a heated blade to melt adhere the part around the sheet of a fluid-absorbing material or to punch out a pad at the part around the sheet of a fluid-absorbing material by melt cutting.

When the part around the sheet of a fluid-absorbing material is melt adhered, a feminine hygienic pad having 3 composite absorption sheets of the present invention can be obtained continuously by punching out the pad at the part around the melt adhered part. In the above process of melt adhesion or melt cutting, an intermediate melt adhesion is formed between the face film of a composite absorption sheet and the backing sheet of another composite absorption sheet disposed above because of the layer of an adhesive placed between the film and the sheet. In the peripheral part of the sheet of a fluid-absorbing material, the temporary attachment between the composite absorption sheets is enhanced. However, the intermediate melt adhesion at the peripheral part of the sheet of a fluid-absorbing material can be peeled off by rubbing by fingers. Because no layer of an agent for preventing melt adhesion is present between the face film and the backing sheet in the same composite absorption sheet, the face film and the backing sheet are tightly adhered together, and the sheet of a fluid-absorbing material can be contained between the face film and the backing sheet with stability. In this construction, peeling off the composite absorption sheet can be made more easily by leaving one short edge in the periphery of the composite absorption sheet without melt adhesion, or by mechanically cutting an edge of the composite absorption sheet in which all peripheral parts have been melt adhered.

A multi-layer feminine hygienic pad having 4 or more layers can also be produced by a similar process as that used for producing the above embodiment.

Because the face films and the backing sheets are temporarily attached together by a heat-sensitive adhesive or a pressure-sensitive adhesive having a small adhesive strength, the composite absorption sheets can be removed successively from an upper sheet to a lower sheet.

As described above, the continuous process of the present invention has the characteristics that a long sheet of the face film of a lower composite absorption sheet and a long sheet of the backing sheet of an upper composite absorption sheet are temporarily attached together in advance, and that the space around the sheet of a fluid-absorbing sheet is heat pressed and then punched out or melt cut by heat.

Figure 11:
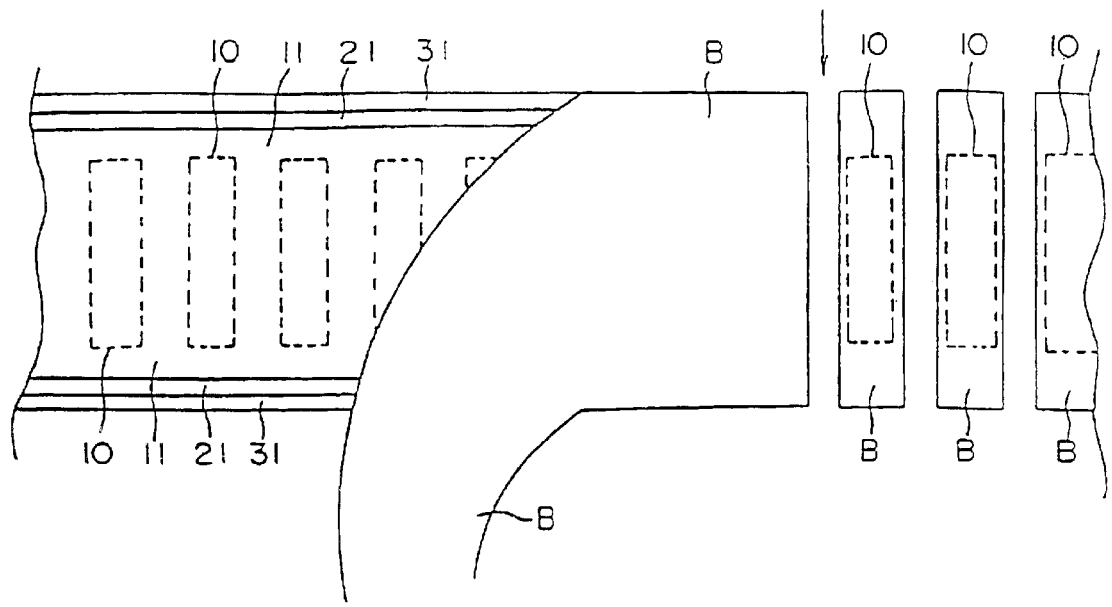
FIG. 11 shows a schematic illustration of the process for producing the multi-layer feminine hygienic pad shown in FIG. 10.

When this embodiment of the feminine hygienic pad is produced in accordance with the above process, for example, the process can be conducted by the following steps. In each of three long continuous laminate sheets for the composite absorption sheets which comprise each a long sheet for the backing sheet 11, 21 or 31 having a different width from each other, sheets of a fluid-absorbing material are disposed on each backing sheet at the same position shown in FIG. 11 (the sheets of a fluid-absorbing material on the lowest backing sheet alone are shown in FIG. 11). The combined long laminate has three sheets of a fluid-absorbing sheet indirectly laid on top of another. The three long sheets are temporarily attached together with a pressure-sensitive adhesive having a small adhesive strength. This laminate sheet is continuously prepared. To the thus prepared continuous laminate sheet, a long sheet of a release film B which is prepared by coating the release film with a releasing agent and a pressure-sensitive adhesive is laminated. The feminine hygienic pads using a pressure-sensitive adhesive having a small adhesive strength shown in FIGS. 10(a) to 10(c) are continuously and efficiently produced by punching out from the laminate sheet obtained above in the manner shown in FIGS. 10(a) to 10(c).

In this feminine hygienic pad, the whole lower side of the lowest backing sheet can tightly be fixed to an underwear with a pressure-sensitive adhesive having a strong adhesive property. In the upper composite absorption sheets, the extended peripheral parts of the backing sheets alone are adhered to the underwear by a strong adhesion, and the central parts are attached to the lower composite absorption sheet with a pressure-sensitive adhesive having a small adhesive strength. Therefore, there is no possibility that the positions of the upper composite absorption sheets shift during use. When an upper composite absorption sheet is removed, the central part of the upper composite absorption sheet is easily peeled off by peeling an end part fixed to the underwear. No transfer of the adhesive to a lower composite absorption sheet takes place.

To this embodiment of the feminine hygienic pad, the other methods of temporary attachment described above can also be used in combination.

Figure 12:
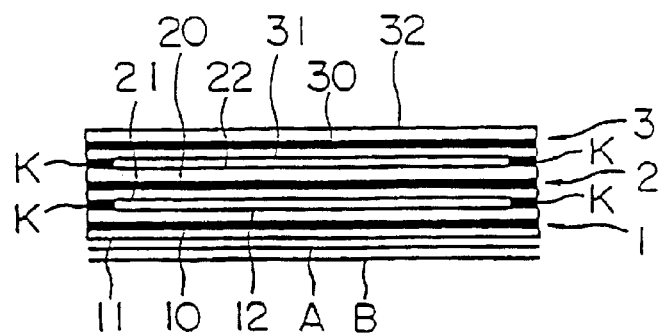
FIG. 12 shows a transverse sectional view of a multi-layer feminine hygienic pad as another embodiment of the present invention.

The embodiment of the feminine hygienic pad shown in FIG. 12 relates to a multi-layer feminine hygienic pad in which the backing sheet has the same dimension as that of the sheet of a fluid-absorbing material. To apply this structure to the feminine hygienic pad of the present invention, the peripheral part of the upper side of a lower composite absorption sheet and a part or the whole of the peripheral part of the lower side of an upper composite absorption sheet are attached together by a temporary attachment K as shown in FIG. 12.

In this case, the methods of temporary attachment used above when the backing sheet has a larger dimension than that of the sheet of a fluid-absorbing material can also be used as the method for the temporary attachment K. For example, the method of adhesion with a pressure-sensitive adhesive which allows repeated adhesion and peeling, the method of intermediate melt adhesion in the presence of an agent for preventing melt adhesion disposed between the sheets to be adhered, the method of using a perforation which facilitates cutting a film, or the method of pressing by a high pressure without using an adhesive can be used. Any conventional method of temporary attachment can be used without particular restriction as long as the adhesive property does not remain on the sheet of a fluid-absorbing material on the lower backing sheet which is used after the upper composite absorption sheet has been removed.

Moreover, when a heat-sensitive adhesive or a pressure-sensitive adhesive having a small adhesive strength is used in this type of the feminine hygienic pad, the lower side of the backing sheet of an upper composite absorption sheet and the upper side of a lower composite absorption sheet can temporarily be attached together at the whole surfaces of both sheets.

When the multi-layer feminine hygienic pad of this type is prepared by lamination, the handling for the peeling can be facilitated by laminating the layers at a slightly staggered position to form steps in the periphery of the layers.

Figure 13:
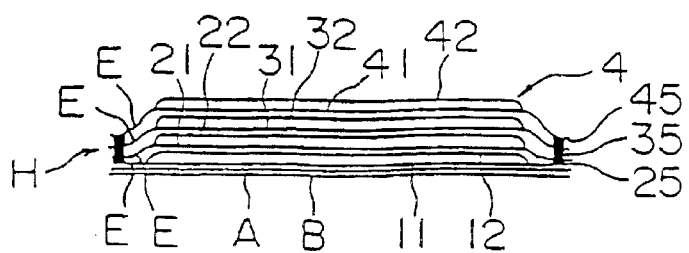
FIG. 13 shows a longitudinal sectional view of a multi-layer feminine hygienic pad as another embodiment of the present invention.

In the feminine hygienic pad shown in FIG. 13, an end part of each composite absorption sheet having a multi-layer structure is made of a film of a thermoplastic resin and the end parts in all composite absorption sheets are fixed to each other by integrally heat sealed part H. A perforation is formed inside the heat sealed part of each composite absorption sheet so that the composite absorption sheets can be peeled off successively from an upper sheet to a lower sheets. As described in this embodiment, one or a combination of two or more of the above methods of temporary attachment can be used in the feminine hygienic pad of the present invention.

In any method of temporary attachment of the present invention, it is advantageous that the length of a backing sheet is made shorter than that of the backing sheet disposed directly above because the uppermost composite absorption sheet can easily be removed by pulling the longest remaining end of the backing sheet.

Figure 14A:
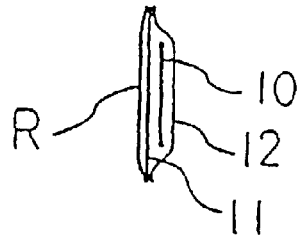
FIGS. 14(a) and 14(b) show a sectional view and a bottom view, respectively, of a composite absorption sheet attached with a packaging film.
Figure 14B:
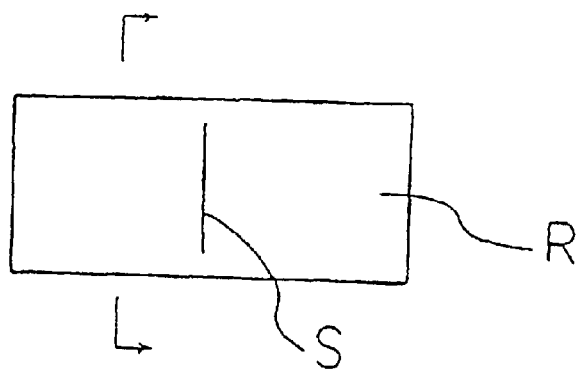

In the feminine hygienic pad shown in FIGS. 14(a) and 14(b), a film R for packaging is additionally attached to the lower side of the backing sheet 11 of the composite absorption sheet (to the left side in FIG. 14(a)). A slit S is formed at the center of the film R (FIG. 14(b)). After the composite absorption sheet is separated, the whole composite absorption sheet can be contained in the film by opening the slit and turning the film inside out. The position and the direction of the slit in the film R is not limited to the central part, and the slit may be formed at any desired position to any desired direction.

Alternatively, an edge of the film for packaging is left unattached to the backing sheet, and the composite absorption sheet is contained in the film by turning the film inside out at the opening formed by the edge left unattached to the backing sheet.

In the process for producing a multi-layer feminine hygienic pad, the multi-layer feminine hygienic pad is produced continuously by using two or more long sheets of a backing sheet made of a thermoplastic resin, two or more long sheets of a porous film of a thermoplastic resin, and two or more sheets of a macromolecular fluid-absorbing material. In a conventional process, composite absorption sheets are separately formed and then laminated by using a method of temporary attachment. The present inventors developed an advantageous process for producing a feminine hygienic pad which comprises preparing a long laminate sheet by laminating a long sheet of a porous film used as the face layer of a lower composite absorption sheet to a long sheet of a backing sheet used as the lowest layer of an upper composite absorption sheet with an adhesive disposed between the long sheets, inserting sheets of a macromolecular fluid-absorbing material between a plurality of the prepared laminate sheets, melt adhering both longitudinal edges of the obtained long laminate sheet by heat sealing or melt cutting, and then cutting the long laminate sheet into parts each containing one sheet of a macromolecular fluid-absorbing material.

When the above process is conducted, the temporarily attachment described above is formed between the long sheet of the porous film used as the face layer of a lower composite absorption sheet and the long sheet for the backing sheet of an upper composite absorption sheet disposed directly above because the adhesive is disposed between the long sheets in the heat sealing step or the melt cutting step. On the other hand, the long sheet for the backing sheet and the long sheet of the porous film on both sides of the same composite absorption sheet are attached together by melt adhesion because no adhesive is disposed between the long sheets, and therefore, the sheet of a macromolecular fluid-absorbing material can be contained between the two long sheets.

As the result, the temporary attachment which enables peeling off individual composite absorption sheets by fingers can be formed continuously and efficiently.

Thus, the present invention has the characteristic that a long laminate sheet is prepared in advance by attaching together a long sheet of a porous film forming the porous film in a composite absorption sheet and a long sheet forming the backing sheet in a composite absorption sheet disposed directly above with an adhesive disposed between the long sheets, and the feminine hygienic pad of the present invention is produced by using the prepared long laminate sheet.

A preferred embodiment of the process of the present invention is described in the following. In the process for continuously producing a multi-layer feminine hygienic pad by using two or more long sheet for the backing sheets made of a thermoplastic resin, two or more long sheets of the porous film made of a thermoplastic resin, and two or more long sheets of a macromolecular fluid-absorbing material, the long sheet of the porous film made of a thermoplastic resin is continuously laid on the upper side of the long sheet for the backing sheet made of a thermoplastic resin, and both longitudinal edges of both sheets are attached together with an adhesive disposed between the edges of the long sheets by pressing the edges of the long sheets to prepare a temporarily attached laminate sheet (lamination of the part indicated by 12 to the part indicated by 21 and the part indicated by 22 to the part indicated by 31 in FIG. 15(*a*)). A plurality of the temporarily attached laminate sheets are prepared in advance.

Figure 15A:
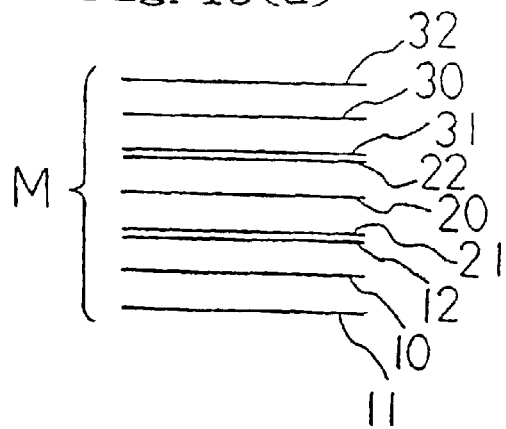
FIG. 15(a) shows a sectional view illustrating the laminate structure of a laminate sheet used in the process of the present invention.
Figure 15B:
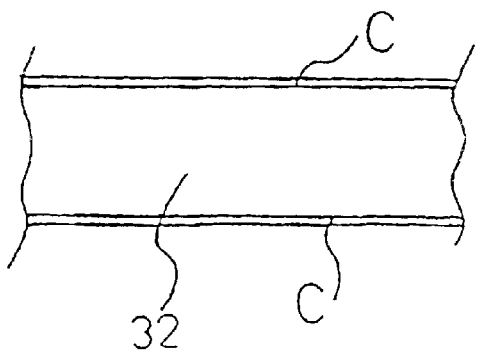
FIG. 15(b) shows a plan view indicating the positions of heat sealing at the side edges, of a laminate sheet in the same process as that used for producing the laminate sheet of the present invention shown in FIG. 15(a).
Figure 15C:
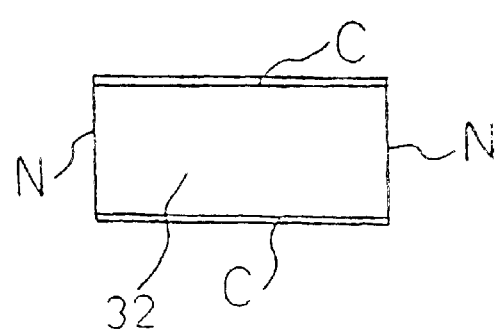
FIG. 15(c) shows a plan view of the multi-layer feminine hygienic pad produced in accordance with the same process as that used for producing the laminate sheet of the present invention shown in FIG. 15(a).

The temporarily attached laminate sheets are alternately placed between two or more long sheets of a macromolecular fluid-absorbing material having a width smaller than that of the temporarily attached laminate sheet, and an alternately laminated sheet M in which the sheets of a macromolecular absorbing sheets and the temporarily attached laminate sheets are alternately laminated together in the manner shown in FIG. 15(*a*) is prepared.

On the uppermost surface of the prepared alternately laminated sheet, one long sheet of a porous film made of a thermoplastic resin for the upper face film is laminated. On the lowest surface of the prepared alternately laminated sheet, one long sheet made of a thermoplastic resin for the backing sheet is laminated. Thus, a long multi-layer laminate sheet containing a prescribed number of the sheet of a macromolecular fluid-absorbing sheet is formed. The longitudinal edges of the long temporarily attached laminate sheets in the long multi-layer laminate sheet are heat sealed or melt cut in the manner shown in FIG. 15(*b*).

At this time, in each long temporarily attached laminate sheet, the edges of the long sheet of a porous film in the long temporarily attached laminate sheet are melt fixed to the corresponding longitudinal edges of the lowest backing sheet disposed below or to the corresponding edges of the backing sheet in another long temporarily attached laminate sheet disposed below, and the edges of the long backing sheet in the long temporarily attached laminate sheet are melt fixed to the corresponding longitudinal edges of the long sheet of a porous film in another long temporarily attached laminate sheet disposed above or to the corresponding edges of the surface porous film made of a thermoplastic resin.

In this step of heat sealing or melt cutting, temporary attachment with intermediate melt adhesion is formed between the longitudinal edges of the long sheet of the porous film made of a thermoplastic resin and the corresponding longitudinal edges of the long sheet made of a thermoplastic resin for the backing sheet disposed directly above in the same temporarily attached laminate sheet by heat sealing or melt cutting in the presence of an adhesive disposed between the long sheets. The prepared long sheet of multi-layer laminate is cut to pieces at the positions separated by the prescribed distance corresponding to the longitudinal length of the feminine hygienic pad to efficiently produce the multi-layer feminine hygienic pad, shown in FIG. 15(*c*).

In this process, the production is facilitated when the sheet of a macromolecular fluid-absorbing material is a long sheet of a fabric.

In the process using the long sheet of a macromolecular fluid-absorbing sheet, the sheet of a macromolecular fluid-absorbing material is exposed at the section N in a multi-layer feminine hygienic pad as shown in FIG. 15(*c*) when the long sheet of the multi-layer laminate sheet is mechanically cut to produce the multi-layer feminine hygienic pad. However, the edges where the sheet of a macromolecular fluid-absorbing material is exposed are longitudinal edges of the obtained feminine hygienic pad. The edges can also be intermediately sealed by the pressure of the mechanical cutting when a substance having a small adhesive strength is impregnated into the materials used in the peripheral parts including the edges. It is also advantageous that the melt cutting is used in the cutting step.

In the process of the present invention, a process in which pieces of a sheet of a macromolecular fluid-absorbing material are prepared by cutting to the size used for the individual feminine hygienic pad and are disposed between the sheets of the laminate at positions separated by a prescribed distance can also be used.

In this process, in the same manner as that of the process described above, a long sheet of a porous film made of a thermoplastic resin is continuously laid on the upper side of a long sheet made of a thermoplastic resin for the backing sheet, and both sheets are attached together by pressing the long sheets with an adhesive disposed between the long sheets to prepare a long laminate sheet. A plurality of these long laminate sheets are prepared where necessary.

Separately, the lower side of another long sheet made of a thermoplastic resin for the backing sheet is coated with a pressure-sensitive adhesive and attached with a release film made of a thermoplastic resin. On this long sheet for the backing sheet, sheets of a macromolecular fluid-absorbing material having a prescribed length which is narrower than the width of the long laminate sheet prepared above are disposed in such a manner that the longitudinal direction of the sheet of a macromolecular fluid-absorbing material is parallel with or perpendicular to the longitudinal direction of the laminate sheet at positions separated by a prescribed distance. On the obtained laminate sheet, another long laminate sheet prepared above is laminated. Sheets of a macromolecular fluid-absorbing material having the prescribed length are disposed on the obtained laminate of the laminates over the corresponding sheets of a macromolecular fluid-absorbing material on the lower laminate sheet. Laminating the above long laminate sheet and disposing the sheets of a macromolecular fluid-absorbing material having the prescribed length are repeated one or more times in accordance with the necessity. Then, a porous film is laminated on the uppermost layer to produce a long composite absorption sheet having the desired number of the sheet of a macromolecular fluid-absorbing material. The prepared long composite absorption sheet is continuously fed to a heat sealing table. There, the above laminate sheets are attached together by heat sealing or melt cutting at the edges outside the sheets of a macromolecular absorbing material. Finally, the sheets of a macromolecular fluid-absorbing material disposed inside the long composite absorption sheet are separated by melt cutting or by heat pressing followed by mechanically cutting the long composite absorption sheet at the parts between the sheets of a macromolecular fluid-absorbing material. When a pressure-sensitive adhesive is applied to a part of the lower side of the sheet of a macromolecular fluid-absorbing material or to the part of the laminate sheet for disposing the sheet of a macromolecular fluid-absorbing material, the sheet of a macromolecular fluid-absorbing material is fixed to the originally disposed position to facilitate the operation in the process. It is also included in the process of the present invention that the sheets of a macromolecular fluid-absorbing material are disposed on individual laminate sheets in advance, and the laminate sheets having the sheets of a macromolecular fluid-absorbing material are then laminated together.

When the above process is conducted, it is necessary that the positions of the sheets of a macromolecular fluid-absorbing material disposed on the laminate sheet be detected by a conventional method, such as the method using a photoelectric tube, and the positions of the sheets of a macromolecular fluid-absorbing material in a plurality of laminate sheets be controlled so that they are brought to the same positions.

In the above process, a release film made of a thermoplastic resin may be attached to the lower side of the lowest backing sheet immediately before the step of the final cutting.

To summarize the advantages of the present invention, in the feminine hygienic pad of the present invention, a plurality of composite absorption sheets are temporarily attached together at the peripheral parts, and the composite absorption sheet can be removed successively from an upper sheet to a lower sheet. Thus, bringing along a number of feminine hygienic pads while staying outside the home is not necessary. For example, when a feminine hygienic pad having two layers is used, the number of the pad brought along is reduced to one half. Similarly, when a feminine hygienic pad having three layers is used, the number is reduced to one third.

When a used sheet of a fluid-absorbing material is removed in a toilet, the position of the backing sheet of the lowest composite absorption sheet fixed to an underwear does not move at all. Therefore, when the fixing is made at a correct position at first, the fresh composite absorption sheet can be provided at the correct position merely by removing the used uppermost composite absorption sheet.

When a conventional feminine hygienic pad is used, the handling for removing a used pad from the underwear and exactly attaching a fresh pad to the underwear is required. In contrast, the multi-layer feminine hygienic pad of the present invention requires removal of one layer alone, and thus provides remarkable advantage of reducing the required time.

What is claimed is:

1. A multi-layer feminine hygienic pad comprising a laminate of two or more composite absorption sheets in which an upper composite absorption sheet which comprises an upper backing sheet laminated to a back side thereof and has an approximately same size as a size of the upper backing sheet is laid on top of a lower composite absorption sheet which comprises a lower backing sheet laminated to a back side thereof and has an approximately same size as a size of the lower backing sheet such that the back side of the upper composite absorption sheet is placed downward, and a peripheral part of the lower backing sheet and a peripheral part of the upper backing sheet are temporarily attached together in a manner consisting of high pressure pressing the peripheral part of the lower backing sheet and the peripheral part of the upper backing sheet without using an adhesive, and a back side of a lowest backing sheet of a lowest composite absorption sheet is capable of being attachable to underwear.

2. The multi-layer feminine hygienic pad according to claim 1, wherein the peripheral part of the lower backing sheet and the peripheral part of the upper backing sheet are temporarily attached together at two opposite edges of the peripheral part of the lower backing sheet and the peripheral part of the upper backing sheet.

3. The multi-layer feminine hygienic pad according to claim 2, wherein the peripheral part of the lower backing sheet and the peripheral part of the upper backing sheet have protrusions and depressions formed by pressing the peripheral parts with a press and are temporarily attached together by fitting the protrusions and the depressions of the lower backing sheet to the depressions and the protrusions of the upper backing sheet, respectively.

4. The multi-layer feminine hygienic pad according to claim 3, wherein the attachment to underwear is provided by attaching a pressure-sensitive adhesive to the back side of the lowest backing sheet of the lowest composite absorption sheet, the pressure-sensitive adhesive being coated on a release film.

5. The multi-layer feminine hygienic pad according to claim 3, wherein the upper composite absorption sheet and the lower composite absorption sheet each have a color different from other sheets.

6. The multi-layer feminine hygienic pad according to claim 4, wherein the upper composite absorption sheet and the lower composite absorption sheet each have a color different from other sheets.

7. The multi-layer feminine hygienic pad according to claim 2, wherein the attachment to underwear is provided by attaching a pressure-sensitive adhesive to the back side of the lowest backing sheet of the lowest composite absorption sheet, the pressure-sensitive adhesive being coated on a release film.

8. The multi-layer feminine hygienic pad according to claim 7, wherein the upper composite absorption sheet and the lower composite absorption sheet each have a color different from other sheets.

9. The multi-layer feminine hygienic pad according to claim 2, wherein the upper composite absorption sheet and the lower composite absorption sheet each have a color different from other sheets.

10. The multi-layer feminine hygienic pad according to claim 1, wherein the peripheral part of the lower backing sheet and the peripheral part of the upper backing sheet have protrusions and depressions formed by pressing the peripheral parts with a press and are temporarily attached together by fitting the protrusions and the depressions of the lower backing sheet to the depressions and the protrusions of the upper backing sheet, respectively.

11. The multi-layer feminine hygienic pad according to claim 10, wherein the attachment to underwear is provided by attaching a pressure-sensitive adhesive to the back side of the lowest backing sheet of the lowest composite absorption sheet, the pressure-sensitive adhesive being coated on a release film.

12. The multi-layer feminine hygienic pad according to claim 11, wherein the upper composite absorption sheet and the lower composite absorption sheet each have a color different from other sheets.

13. The multi-layer feminine hygienic pad according to claim 10, wherein the upper composite absorption sheet and the lower composite absorption sheet each have a color different from other sheets.

14. The multi-layer feminine hygienic pad according to claim 1, wherein the attachment to underwear is provided by attaching a pressure-sensitive adhesive to the back side of the lowest backing sheet of the lowest composite absorption sheet, the pressure-sensitive adhesive being coated on a release film.

15. The multi-layer feminine hygienic pad according to claim 14, wherein the upper composite absorption sheet and the lower composite absorption sheet each have a color different from other sheets.

16. The multi-layer feminine hygienic pad according to claim 1, wherein the upper composite absorption sheet and the lower composite absorption sheet each have a color different from other sheets.

* * * * *